(12) United States Patent
Song et al.

(10) Patent No.: US 12,398,418 B2
(45) Date of Patent: Aug. 26, 2025

(54) SIMULTANEOUS SINGLE-MOLECULE EPIGENETIC IMAGING OF DNA METHYLATION AND HYDROXYMETHYLATION

(71) Applicant: THE BOARD OF TRUSTEES OF THE LELAND STANFORD JUNIOR UNIVERSITY, Stanford, CA (US)

(72) Inventors: Chunxiao Song, Oxford (GB); Stephen R. Quake, Stanford, CA (US); Axel Brunger, Stanford, CA (US); Jiajie Diao, Stanford, CA (US)

(73) Assignee: The Board of Trustees of the Leland Stanford Junior University

( * ) Notice: Subject to any disclaimer, the term of this patent is extended or adjusted under 35 U.S.C. 154(b) by 513 days.

(21) Appl. No.: 17/537,290

(22) Filed: Nov. 29, 2021

(65) Prior Publication Data

US 2022/0403449 A1    Dec. 22, 2022

Related U.S. Application Data

(63) Continuation of application No. 15/470,635, filed on Mar. 27, 2017, now abandoned.

(60) Provisional application No. 62/324,161, filed on Apr. 18, 2016.

(51) Int. Cl.
*C12Q 1/68* (2018.01)
*C12Q 1/6818* (2018.01)
*C12Q 1/6834* (2018.01)

(52) U.S. Cl.
CPC ......... *C12Q 1/6818* (2013.01); *C12Q 1/6834* (2013.01)

(58) Field of Classification Search
USPC .............. 435/6.1, 6.11, 91.1, 183; 436/94; 536/23.1, 24.3
See application file for complete search history.

(56) References Cited

U.S. PATENT DOCUMENTS

| | | |
|---|---|---|
| 8,741,567 B2 | 6/2014 | He et al. |
| 9,034,597 B2 | 5/2015 | Bitinaite et al. |
| 9,040,239 B1 | 5/2015 | Zheng et al. |
| 9,115,386 B2 | 8/2015 | Rao et al. |
| 9,175,338 B2 | 11/2015 | Flusberg et al. |
| 9,175,341 B2 | 11/2015 | Flusberg et al. |
| 9,175,348 B2 | 11/2015 | Korlach et al. |
| 9,290,807 B2 | 3/2016 | Booth et al. |
| 9,447,452 B2 | 9/2016 | Rao et al. |
| 9,598,731 B2 | 3/2017 | Talasaz |
| 9,816,986 B2 | 11/2017 | Rao et al. |
| 9,834,822 B2 | 12/2017 | Talasaz |
| 2006/0281122 A1 | 12/2006 | Bryant et al. |
| 2010/0143929 A1 | 6/2010 | Levenson et al. |
| 2010/0273151 A1 | 10/2010 | Tapscott et al. |
| 2011/0301045 A1 | 12/2011 | He et al. |
| 2012/0034685 A1 | 2/2012 | Sparks et al. |
| 2012/0122087 A1 | 5/2012 | Li et al. |
| 2012/0301881 A1 | 11/2012 | Zhu et al. |
| 2013/0034546 A1 | 2/2013 | Rava et al. |
| 2014/0057264 A1 | 2/2014 | Chun et al. |
| 2014/0127678 A1 | 5/2014 | Guan et al. |
| 2014/0322707 A1 | 10/2014 | He et al. |
| 2014/0363815 A1 | 12/2014 | Dahl et al. |
| 2015/0011403 A1 | 1/2015 | Lo et al. |
| 2015/0011408 A1 | 1/2015 | Kester |
| 2015/0051113 A1 | 2/2015 | Kim |
| 2016/0122831 A1 | 5/2016 | West |
| 2016/0145685 A1 | 5/2016 | Jensen et al. |
| 2016/0340740 A1 | 11/2016 | Zhang |
| 2017/0253924 A1 | 9/2017 | Lu et al. |
| 2018/0046754 A1 | 2/2018 | Batagov et al. |
| 2020/0224190 A1 | 7/2020 | Song et al. |

FOREIGN PATENT DOCUMENTS

| | | |
|---|---|---|
| WO | 2010114599 A1 | 10/2010 |
| WO | 2014082032 A1 | 5/2014 |
| WO | 2014168711 A1 | 10/2014 |
| WO | 2014191981 A1 | 12/2014 |
| WO | 2015145133 A1 | 1/2015 |
| WO | 2015021282 A1 | 2/2015 |
| WO | 2015104302 A1 | 7/2015 |
| WO | 2017176630 A1 | 10/2017 |

OTHER PUBLICATIONS

Zhou, et al. "A Pilot Study of Next-Generation Sequencing on Cell-Free DNA from Blood Plasma and Bone Marrow Fluid for Detecting Leukemic Clonal Abnormalities," North American J. Med. and Science (2014): vol. 7 No.4, 180-185.
Fan et al. "Analysis of the Size Distributions of Fetal and Maternal Cell-Free DNA by Paired-End Sequencing," Clinical Chemistry (2010): 56(8), 1279-1286.
Globisch, et al. "Tissue Distribution of 5-Hydroxymethylcytosine and Search for Active Demethylation Intermediates," PLOS ONE (2010): 5(12), e15367.
Song, et al. "5-Hydroxymethylcytosine signatures in cell-free DNA provide information about tumor types and stages," Cell Research (2017): 27, 1231-1242.
Mellen et al., "MeCP2 binds to 5hmc enriched within active genes and accessible chromatin in the nervous system," Cell (2012): 151(7), 1417-1430.
Thomson, el al. "Comparative analysis of affinity-based 5-hydroxymethylalion enrichment techniques," Nucleic Acids Research (2013): 41(22), e206.

(Continued)

*Primary Examiner* — Frank W Lu
(74) *Attorney, Agent, or Firm* — Rimon Law

(57) ABSTRACT

Provided herein is a method for analyzing genomic DNA In some embodiments, the method may comprise labeling a genomic sample by adding a capture tag to the ends of the DNA molecules in the sample and labeling molecules that comprise hydroxymethylcytosine with a first fluorophore, immobilizing the labeled DNA molecules on a support, and imaging individual molecules of hydroxymethylated genomic DNA on the support.

4 Claims, 10 Drawing Sheets

Specification includes a Sequence Listing.

(56) References Cited

OTHER PUBLICATIONS

Cui, et al. "JBP1-seq: A fast and efficient method for genome-wide profiling of 5hmC," Genomics (2014): vol. 104, Issue 5, 368-375.
Han, et al. "A Highly Sensitive and Robust Method for Genome-wide 5hmC Profiling of Rare Cell Populations," Molecular Cell (2016): vol. 63, No. 4, 711-719.
Gromminger, et al. "Fetal aneuploidy detection by cell-free DNA sequencing for multiple pregnancies and quality Issues with vanishing twins," Journal of Clinical Medicine (2014): vol. 3, No. 4, 679-692.
Tetruashvili, NK et al. "Non-invasive prenatal diagnosis of aneuploidy by sequencing extracellular DNA, Modern view of the problem," Scientific and practical journal (2014): No. 10, 4-7.
Volik, "Cell-free DNA (cfDNA): Clinical Significance and Utility in Cancer Shaped by Emerging Technologies," Molecular Cancer Research (2016): 14(10), 898-908.
Da Costa, et al. "Detection of cancer-specific epigenomic chagnes in biofuluids: Powerful tools in biomarker discovery and application, " Molecular Oncology (20132) vol. 6, 704.
Park et al., "Detection of DNA adducts by high-performance liquid chromatography with electrochemical detection", Carcinogenesis, 1989, vol. 10, No. 5, pp. 827-832.
Castro et al., "5-Methylcytosine attack by hydroxyl free radicals and during carbon tetrachloride promoted liver microsomal lipid peroxidation: structure of reaction products", Chemico-Biological Interactions, 1996, 99, pp. 289-299.
Song et al., "Specific Method for the Determination of Genomic DNA Methylation by Liquid Chromatography-Electrospray Ionization Tandem Mass Spectrometry", Anal. Chem., 2005, 77, pp. 504-510.
Tanaka et al., "Development of fluorescence-labeling method for methylcytosine with metal complexation," Nucleic Acids Symposium Series, 2006, No. 50, pp. 135-136.
Tanaka et al., "Direct Labeling of 5-Methylcytosine and Its Applications," J. Am. Chem. Soc., 2007, 129, pp. 5612-5620.
Jin et al., "Examination of the Specificity of DNA Methylation Profiling Techniques towards 5-Methylcytosine and 5-Hydroxymethylcytosine," Nuc. Acids Res., 2010, vol. 38, No. 11, pp. 1-7.
Song, et al., "Selective chemical labeling reveals the genome-wide distribution of 5-hydroxymethylcytosine", Nature Biotechnology, Jan. 2011, vol. 29, No. 1, pp. 68-72.
Song, et al., "Sensitive and specific single-molecule sequencing of 5-hydroxymethylcytosine", Nat. Methods, Jan. 2012, vol. 9, Issue 1, pp. 75-77.
Song, et al., "Mapping new nucleotide variants in the genome and transcriptome", Nature Biotechnology, Nov. 2012, vol. 30(11), pp. 1107-1116.
Zhang et al., "Tet-mediated covalent labelling of 5-methylcytosine for its genome-wide detection and sequencing," Nature Communications, 2013, vol. 4, 1517, pp. 1-10.
Li, et al., "5'-methylcytosine and 5'-hydroxymethylcytosine Each Provide Epigenetic Information to the Mouse Zygote", PLoS One, May 2013, vol. 8, Issue 5, e63689.
Newmen, et al., "An ultrasensitive method for quantitating circulating tumor DNA with broad patient coverage," Nature Medicine, May 2014, vol. 20, No. 5, pp. 548-554.
Nifker et al., "One-Pot Chemoenzymatic Cascade for Labeling of the Epigenetic Marker 5-Hydroxymethylcytosine", ChemBiochem., Sep. 7, 2015, vol. 16, Issue 13, pp. 1857-1860.
Wei et al., "Rapid Short-Read Sequencing and Aneuploidy Detection Using MinION Nanopore Technology," Genetics, Jan. 2016, vol. 202, Issue 1, pp. 37-44.
Song, et al., "Simultaneous single-molecule epigenetic imaging of DNA methylation and hydroxymethylation", PNAS, Apr. 19, 2016, vol. 113, No. 16, pp. 4338-4343.
Unknown, "DNA Fragmentation," New England Biolabs, printed on Jan. 16, 2020.
Chiu, et al. "Non-invasive prenatal assessment of trisomy 21 by multiplexed maternal plasma DNA sequencing: large scale validity study," British Medical Journal (2011): vol. 342, No. 7401, 1-9.
Feng, et al. "Conservation and divergence of methylation patterning in plants and animals," Proceedings of the National Academy of Sciences (2010): vol. 107, No. 19, 8689-8694.

FIG. 3A
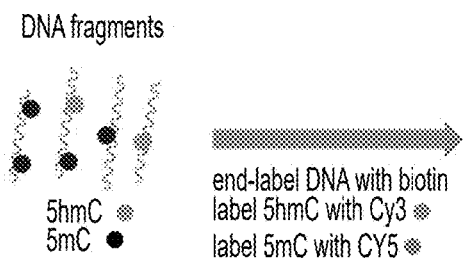
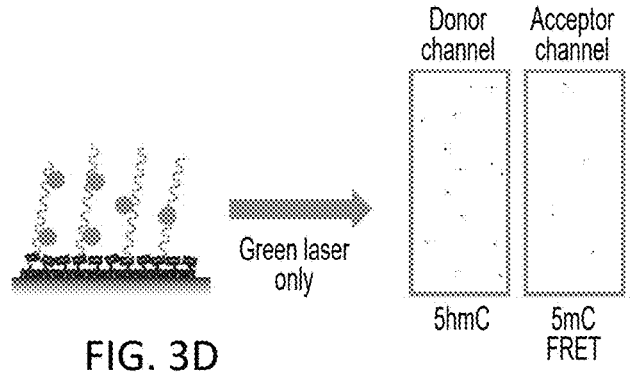
FIG. 3B
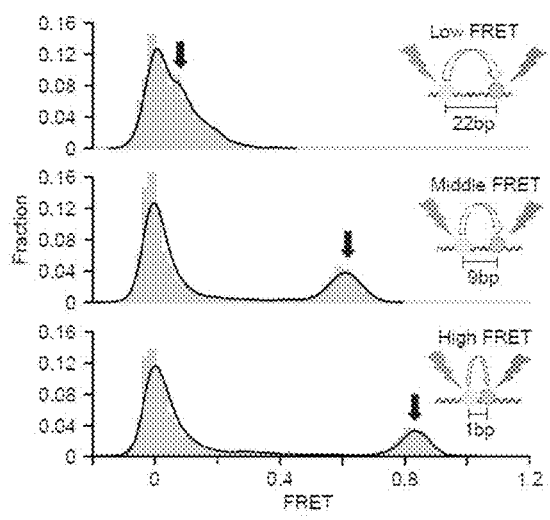
FIG. 3D
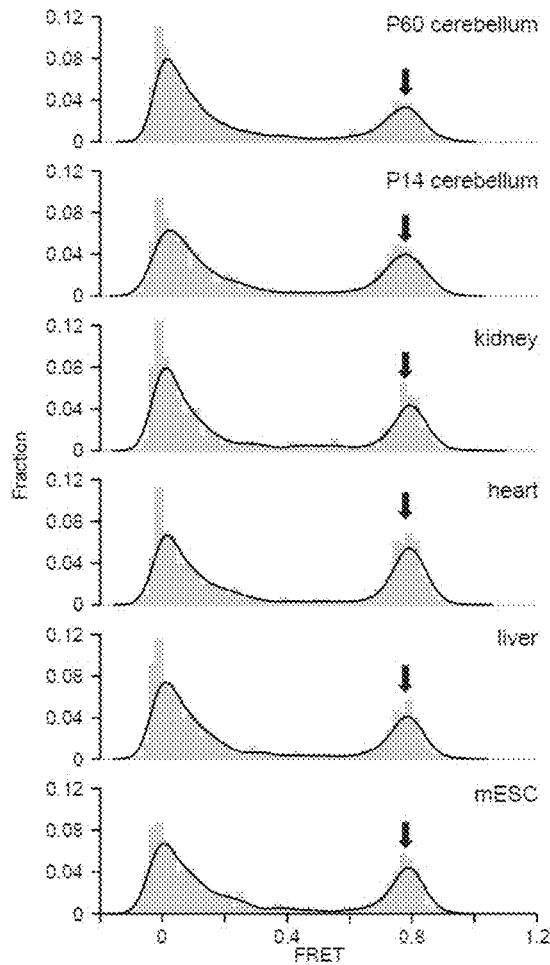
FIG. 3C
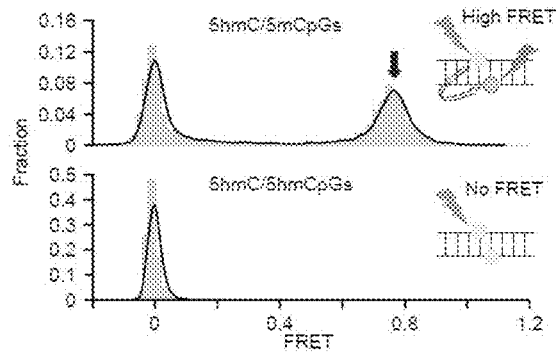

FIG. 9A
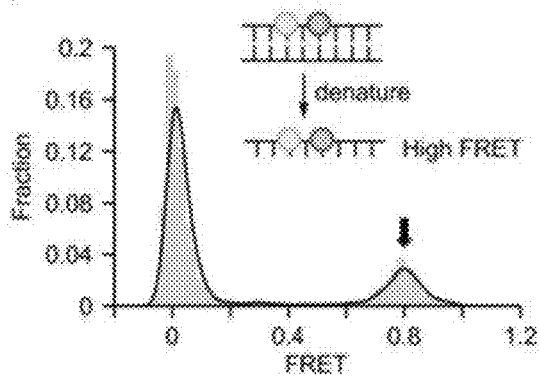 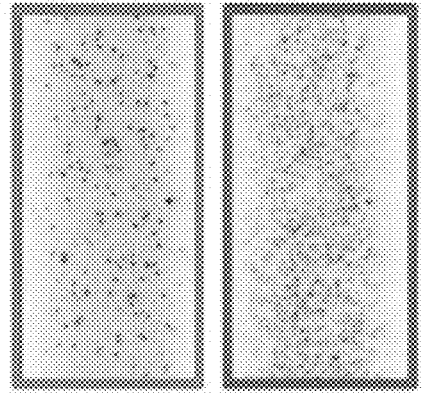
FIG. 9B
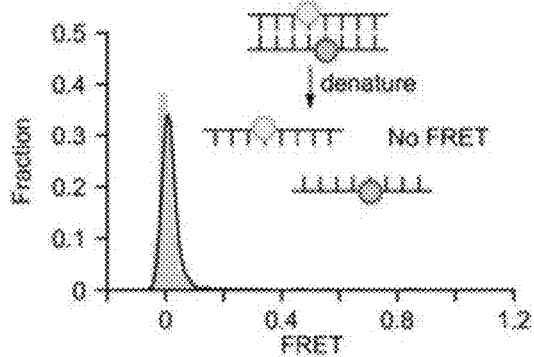 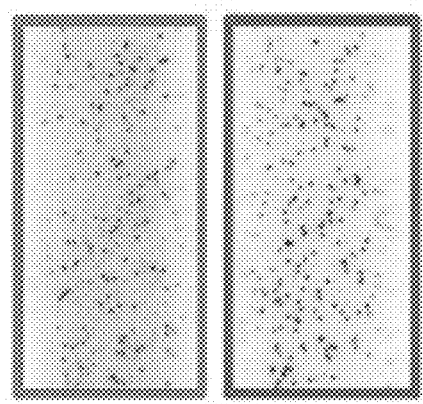
FIG. 9C
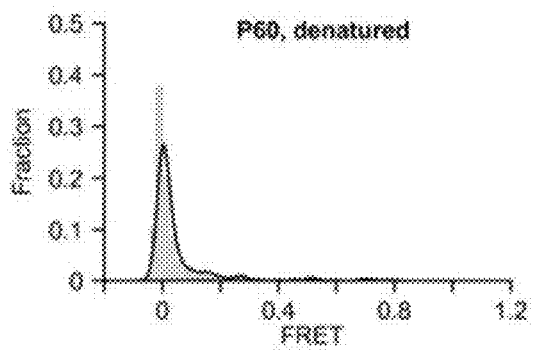 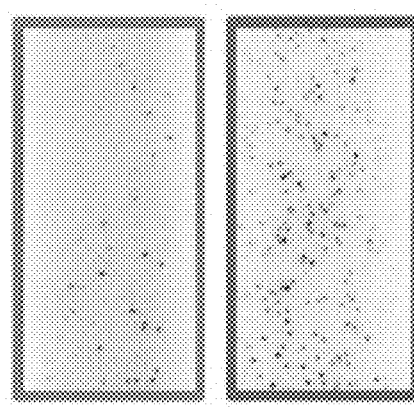
FIG. 9D
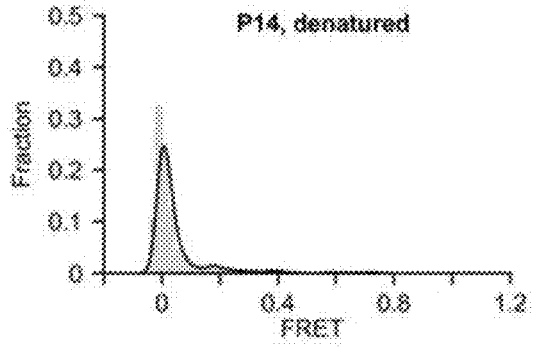 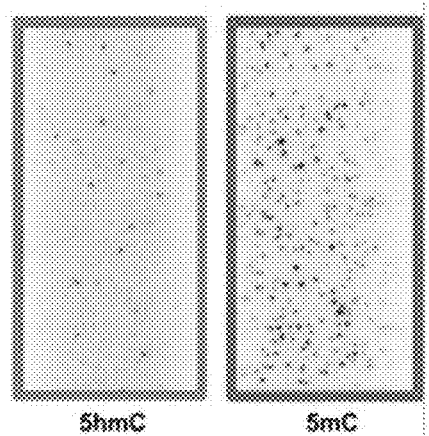

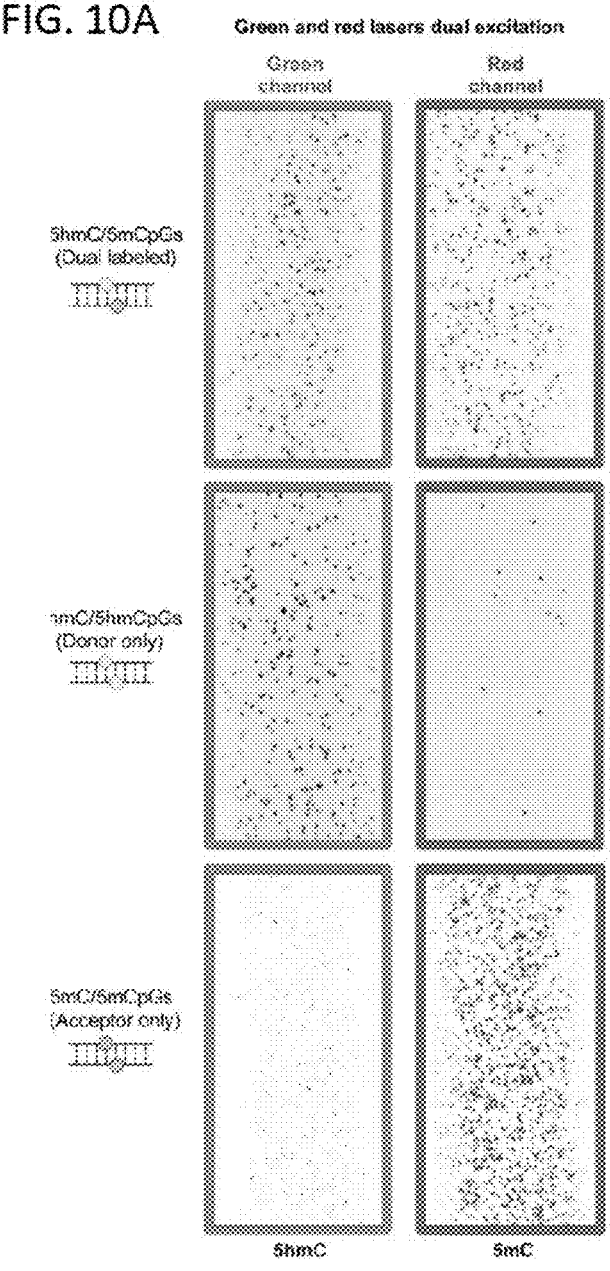
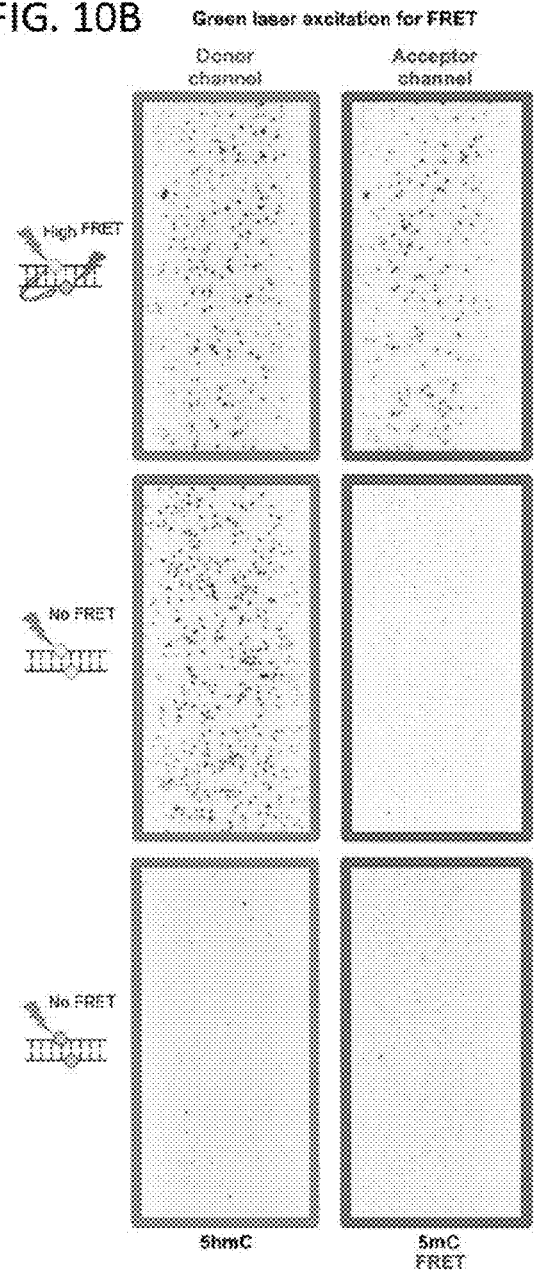

SIMULTANEOUS SINGLE-MOLECULE EPIGENETIC IMAGING OF DNA METHYLATION AND HYDROXYMETHYLATION

CROSS-REFERENCING

This application is a Continuation application of U.S. application Ser. No. 15/470,635, filed Mar. 27, 2017, now abandoned, which application is incorporated by reference herein. This application also claims the benefit of U.S. provisional application Ser. No. 62/324,161, filed on Apr. 18, 2016, which application is incorporated by reference herein.

GOVERNMENT RIGHTS

This invention was made with Government support under contract W81:XWH-11-1-0287 awarded by the Department of Defense and under contract CA154209 awarded by the National Institutes of Health. The Government has certain rights in the invention.

BACKGROUND

Epigenetic modifications of DNA contribute critical regulatory functions to the underlining genetic sequence. 5-Methylcytosine (5mC) and 5-hydroxymethylcytosine (5hmC) are the two major DNA modifications in the mammalian genome and are often referred to as the "fifth base" and "sixth base", respectively. 5mC is generated by DNA methyltransferase (DNMTs) mainly at CpG dinucleotides and generally results in gene silencing. 5hmC is oxidized from 5mC by ten-eleven translocation (TET) family dioxygenases and mostly enriched in brain. 5hmC is generally believed to be a gene activation mark for two reasons. First, it is enriched in active genes in brain and other tissues. Second, 5hmC is the key intermediate in the mammalian active DNA demethylation pathway in which 5hmC is further oxidized by TET to 5-formylcytosine (5fC) and 5-carboxylcytosine (5caC) followed by removal of 5fC and 5caC through base excision repair.

Intensive research on 5hmC in recent years indicated the TET-mediated oxidation process plays important roles in diverse biological processes ranging from embryonic development to carcinogenesis; however, how 5hmC exerts its biological role is largely unclear. One important piece of information that has been missing is the interplay between 5hmC and its precursor 5mC. Despite many techniques which have been developed to detect and sequence 5mC and 5hmC, including recent advances in base-resolution mapping of 5hmC no method to date can simultaneously reveal 5mC and 5hmC sites in the same DNA molecule.

Presented herein is a new ultra-sensitive single-molecule imaging technology capable of detecting and quantifying 5mC and 5hmC from trace samples, which can be used to study the distance relationship between 5mC and 5hmC with single-molecule fluorescence resonance energy transfer (smFRET).

SUMMARY

Provided herein is a method for analyzing genomic DNA In some embodiments, the method may comprise labeling a sample comprising the genomic DNA by adding a capture tag to the ends of the DNA molecules in the sample and labeling molecules that comprise hydroxymethylcytosine with a first fluorophore; immobilizing the labeled DNA molecules on a support; and imaging individual molecules of hydroxymethylated genomic DNA on the support. In some embodiments, a second fluorophore can be added to molecules that comprise methylcytosine, thereby providing a way to examine hydroxymethylation and methylation at a single molecule resolution.

The method generally employs a selective chemical labeling strategy to label DNA base modifications with specific fluorophores, followed by single-molecule imaging fluorescent assays. The method is highly modular and can be used to image just one modification (e.g., 5hmC) or multiple modifications (e.g., 5hmC and 5mC). For example, to image 5hmC, the DNA fragments can be first end-labeled with capture tag (e.g., a biotin) and a fluorophore using a terminal transferase (TdT) and a modified (e.g., biotinylated and/or fluorescent) nucleotides. The capture tag is used to immobilize DNA molecules to the microscope slide and the fluorophore serves as a counter for total amount of DNA Next the 5hmC in the can be labeled with a distinguishable fluorophore. In this example, the labeled biotinylated DNA can be captured by surface-tethered neutravidin on a passivated microscope slide and imaged with single-molecule total internal reflection fluorescence (TIRF) microscopy. Likewise, to image 5mC and 5hmC simultaneously, a dual-labeling strategy can be employed. In this method, DNA fragments are end-labeled with a capture tag and the 5hmC was labeled with a fluorophore as described above. Then, the 5mC is labeled with a second, distinguishable fluorophore. The number of 5hmC and 5mC modifications can be determined by counting each fluorophores. In addition, single-molecule fluorescence resonance energy transfer (smFRET) can be used to measure the proximity between 5mC and 5hmC in the same DNA molecule.

Among other things, the data obtained from the method can be used as a diagnostic, theranostic or prognostic for a variety of diseases or conditions, for example.

These and other features of the present teachings are set forth herein.

BRIEF DESCRIPTION OF THE FIGURES

The skilled artisan will understand that the drawings, described below, are for illustration purposes only. The drawings are not intended to limit the scope of the present teachings in any way FIG. 1A. Single-molecule imaging of 5hmC. General procedure for single-molecule imaging of 5hmC. DNA fragments are end-labeled with biotin and Cy3 and 5hmC is labeled with Cy5. The labeled DNA is immobilized to the microscope slide and imaged with single molecule TIRF microscopy.

FIG. 3A. smFRET analysis between dual-labeled 5mC and 5hmC. General procedure for smFRET analysis between 5mC and 5hmC. DNA fragments are end-labeled with biotin, 5hmC is labeled with Cy3 and 5mC is labeled with Cy5. The labeled DNA is immobilized to the microscope slide and imaged with single-molecule TIRF microscopy for smFRET analysis.

FIG. 3B. smFRET analysis between dual-labeled 5mC and 5hmC. smFRET distributions of dual-labeled synthetic DNA with 5mC and 5hmC separated with different length in the same DNA strand. Solid lines indicate the Gaussian kernel density estimation. Arrows indicate FRET peaks. The zero FRET peak is mainly from DNAs with donor only.

FIG. 3C. smFRET analysis between dual-labeled 5mC and 5hmC. smFRET distributions of dual-labeled synthetic DNA with 5hmC/5mCpG or 5hmC/5hmCpG sites. Solid lines indicate the Gaussian kernel density estimation. Arrows indicate FRET peaks. The zero FRET peak is mainly from DNAs with donor only.

FIG. 3D. smFRET analysis between dual-labeled 5mC and 5hmC. smFRET distributions of dual-labeled mouse genomic DNA from various tissues and mESC. Solid lines indicate the Gaussian kernel density estimation. Arrows indicate FRET peaks. The zero FRET peak is mainly from DNAs with donor only.

FIG. 9A. smFRET distributions and example images of denatured samples. Denatured dual-labeled synthetic DNA with 5mC and 5hmC separated with 1bp in the same strand.

FIG. 9B. smFRET distributions and example images of denatured samples. Denatured dual-labeled synthetic DNA with 5hmC/5mCpG site.

FIG. 9C. smFRET distributions and example images of denatured samples. Denatured dual-labeled mouse P60 cerebellum genomic DNA.

FIG. 9D. smFRET distributions and example images of denatured samples. Denatured dual-labeled mouse P14 cerebellum genomic DNA Each panel has smFRET distribution on the left, and dual excitation example images on the right showing the fluorophore labeling remains after denaturing. Arrows indicate FRET peak.

FIG. 10A. Example images of model DNA with different CpG sites. Green and red lasers dual excitation.

FIG. 10B. Example images of model DNA with different CpG sites. Green laser excitation only smFRET experiments of model DNA with different CpG sites. Top row: example image of model DNA containing a 5hmC/5mCpG site. Middle row: example image of model DNA containing a 5hmC/5hmCpG site. Bottom row: example image of model DNA containing a 5mC/5mCpG site.

DEFINITIONS

Figure 1A:
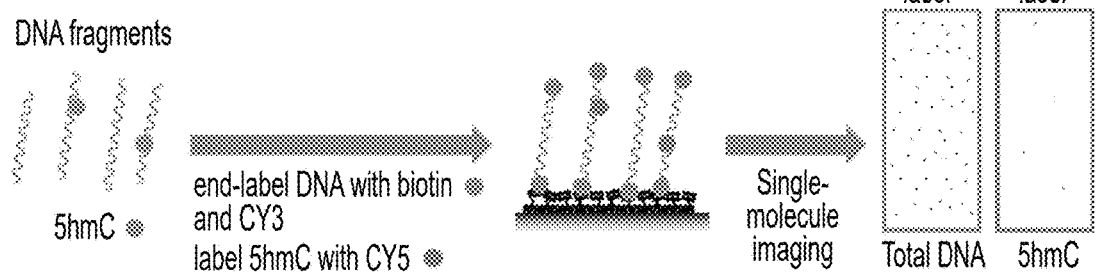
FIG. 1B. Single-molecule imaging of 5hmC. Fluorophore counts of labeled P60 and P14 mouse cerebellum genomic DNA with example images shown on the right.
FIG. 1C. Single-molecule imaging of 5hmC. Distribution of multiple fluorophores on DNA fragment of mouse cerebellum when detecting 5hmC.
FIG. 1D. Single-molecule imaging of 5hmC. 5hmC level of mouse cerebellum DNA Error bars, mean±SD (n=15 counting regions).

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

The term "sample" as used herein relates to a material or mixture of materials, typically, although not necessarily, in liquid form, containing one or more analytes of interest.

The term "nucleic acid sample," as used herein denotes a sample containing nucleic acids. Nucleic acid samples used herein may be complex in that they contain multiple different molecules that contain sequences. Genomic DNA from a mammal (e.g., mouse or human) are types of complex samples. Complex samples may have more then 104, 105, 106 or 107 different nucleic acid molecules. A DNA target may originate from any source such as genomic DNA, or an artificial DNA construct. Any sample containing nucleic acid, e.g., genomic DNA made from tissue culture cells or a sample of tissue, may be employed herein.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine (G, C, A and T, respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A form duplexes. LNA nucleotides can be mixed with DNA or RNA residues in the oligonucleotide whenever desired. The term "unstructured nucleic acid," or "UNA," is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively.

Unstructured nucleic acid is described in US20050233340, which is incorporated by reference herein for disclosure of UNA Also included in this definition are ZNAs, i.e., zip nucleic acids.

The term "duplex," or "duplexed," as used herein, describes two complementary polynucleotides that are base-paired, i.e., hybridized together.

The terms "determining," "measuring," "evaluating," "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

A "plurality" contains at least 2 members. In certain cases, a plurality may have at least 10, at least 100, at least 100, at least 10,000, at least 100,000, at least 106, at least 107, at least 108 or at least 109 or more members.

If two nucleic acids are "complementary," each base of one of the nucleic acids base pairs with corresponding nucleotides in the other nucleic acid. Two nucleic acids do not need to be perfectly complementary in order to hybridize to one another.

The term "strand" as used herein refers to a nucleic acid made up of nucleotides covalently linked together by covalent bonds, e.g., phosphodiester bonds. In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "covalently linking" refers to the production of a covalent linkage between two separate molecules.

As used herein, the term "cell-free DNA" refers to DNA that is circulating in the peripheral blood of a patient. The DNA molecules in cell-free DNA may have a median size that is below 1 kb (e.g., in the range of 50 bp to 500 bp, 80 bp to 400 bp, or 100-1,000 bp), although fragments having a median size outside of this range may be present. Cell-free DNA may contain circulating tumor DNA (ctDNA), i.e., tumor DNA circulating freely in the blood of a cancer patient or circulating fetal DNA (if the subject is a pregnant female). cIDNA can be highly fragmented and in some cases can have a mean fragment size about 165-250 bp (Newman et al Nat Med. 2014 20: 548-54). cIDNA can be obtained by centrifuging whole blood to remove all cells, and then isolating the DNA from the remaining plasma or serum. Such methods are well known (see, e.g., Lo et al, Am J Hum Genet 1998; 62:768-75)

As used herein, the term "UDP glucose modified with chemoselective group" refers to a UDP glucose that has been functionalized, particularly at the 6-hydroxyl position, to include a group that is capable of participating in a 1,3 cycloaddition (or "click") reaction. Such groups include azido and alkynyl (e.g., cyclooctyne) groups, although others are known (Kolb et al., 2001; Speers and Cravatt, 2004;

Sletten and Bertozzi, 2009). UDP-6-N3-Glu is an example of a UDP glucose modified with a chemoselective group, although others are known.

As used herein, the term "biotin moiety" refers to an affinity tag that includes biotin or a biotin analogue such as desthiobiotin, oxybiotin, 2-iminobiotin, diaminobiotin, biotin sulfoxide, biocytin, etc. Biotin moieties bind to streptavidin with an affinity of at least 10-8 M.

As used herein, the terms "cycloaddition reaction" and "click reaction" are described interchangeably to refer to a 1,3-cycloaddition between an azide and alkyne to form a five membered heterocycle. In some embodiments, the alkyne may be strained (e.g., in a ring such as cyclooctyne) and the cycloaddition reaction may done in copper free conditions. Dibenzocyclooctyne (DBCO) and difluorooctyne (DIFO) are examples of alkynes that can participate in a copper-free cycloaddition reaction, although other groups are known. See, e.g., Kolb et al (Drug Discov Today 2003 8: 1128-113), Baskin et al (Proc. Natl. Acad. Sci. 2007 104: 16793-16797) and Sletten et al (Accounts of Chemical Research 2011 44: 666-676) for a review of this chemistry.

As used herein, the term "support that binds to biotin" refers to a support (e.g., a planar support such as a microscope slide) that is linked to streptavidin or avidin, or a functional equivalent thereof (e.g., neutravidin).

As used herein, the term "area", in the context of an area of a substrate or an area of an image, refers to a contiguous or non-contiguous area. For example, if a method involves counting the number of labeled DNA molecules in an area, the area in which the labeled DNA molecules are counted may be a single, contiguous space or multiple non-contiguous spaces.

As used herein, the term "imaging" refers to a process by which optical signals from the surface of an object are detected and stored as data in association with a location (i.e., a "pixel"). A digital image of the object can be reconstructed from this data. An area of a membrane may be imaged using a single image or one or more images.

As used herein, the term "individual DNA molecules" refers to individual DNA molecules that are labeled and spatially distinguishable from other DNA molecules.

As used herein, the term "counting" refers to determining the number of individual objects in a greater collection. "Counting" requires detecting separate signals from individual objects in a plurality and then determining how many objects there are in the plurality by counting the individual signals. In the context of the present method, "counting" is done by determining the number of individual signals on a substrate.

Other definitions of terms may appear throughout the specification.

DESCRIPTION OF EXEMPLARY EMBODIMENTS

Provided herein is a way for analyzing DNA methylation and hydroxymethylation in a genomic sample. The method can be employed to analyze genomic DNA from virtually any eukaryotic organism, including, but not limited to such as plants, animals (e.g., reptiles, mammals, insects, worms, fish, etc.), fungi (e.g., yeast), etc. as well as genomic DNA isolated from tissue samples. In certain embodiments, the genomic DNA used in the method may be derived from a mammal, wherein in certain embodiments the mammal is a human. In exemplary embodiments, the sample may contain genomic DNA from a mammalian cell, such as a human, mouse, rat, or monkey cell. The sample may be made from cultured cells or cells of a clinical sample, e.g., a tissue biopsy, scrape or lavage or cells of a forensic sample. In particular embodiments, the nucleic acid sample may be obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lactal duct fluid, lymph, sputum, synovial fluid, urine, amniotic fluid, and semen. In particular embodiments, a sample may be obtained from a subject, e.g., a human. In particular embodiments, the genomic DNA used in the method may be cell-free DNA (cIDNA) refers to DNA that is circulating in the peripheral blood of a subject, e.g., a human. Methods for extracting DNA from such samples are well known.

In some embodiments, the sample comprises DNA fragments obtained from a clinical sample, e.g., a patient that has or is suspected of having a disease or condition such as a cancer, inflammatory disease or pregnancy. In some embodiments, the sample may be made by extracting fragmented DNA from a fresh or archived patient sample, e.g., a formalin-fixed paraffin embedded tissue sample. In other embodiments, the patient sample may be a sample of cell-free circulating DNA from a bodily fluid, e.g., peripheral blood. The DNA fragments used in the initial steps of the method should be non-amplified DNA and, in certain embodiments, has not been denatured beforehand.

The sample may be fragmented mechanically (e.g., by sonication, nebulization, or shearing) or enzymatically, using a double stranded DNA fragmentase enzyme (New England Biolabs, Ipswich Mass.). In other embodiments, the DNA in the initial sample may already be fragmented (e.g., as is the case for FFPE samples and cIDNA, e.g., ctDNA (circulating tumor DNA)).

In some embodiments, the fragments in the initial sample may have a median size that is below 1 kb (e.g., in the range of 50 bp to 500 bp, 80 bp to 400 bp, or 100-1,000 bp), although fragments having a median size outside of this range may be used. Cell-free or circulating tumor DNA (ctDNA), i.e., tumor DNA circulating freely in the blood of a cancer patient, is highly fragmented, with a mean fragment size about 165-250 bp (Newman et al Nat Med. 2014 20: 548-54). cIDNA can be obtained by centrifuging whole blood to remove all cells, and then analyzing the remaining plasma.

After isolation and optional fragmentation of the genomic sample, the sample may be labeled by: (i) adding a capture tag to the ends of the DNA molecules in the sample; and (ii) labeling molecules that comprise hydroxymethylcytosine with a first fluorophore. This step of the method may be done as a single reaction or in consecutive reactions. In this step, the capture tag may be added to the to the ends of the DNA molecules by incubating the sample with a terminal transferase and a nucleotide that is linked to the capture tag (e.g., a biotinylated nucleotide), although the same result can be obtained by incubating the sample with a polymerase and a nucleotide that is linked to the capture tag. If terminal transferase is used, the DNA molecules may be tailed with a run of Gs, As, Ts or Cs added on the 3' end of a strand of the DNA molecules by the action of a terminal transferase. Depending on whether natural nucleotides (G, A, T or C) or fluorescently labeled nucleotides are added to the reaction, a tail may have as few as 1 up to 100 nucleotides. The added capture tag serves to anchor the DNA molecules to a support. In some embodiments, the labeled genomic sample is labeled by: i. universally end-labeling the genomic DNA in the sample with a modified nucleotide comprising a capture tag, thereby adding the capture tag to the ends of the DNA molecules in the sample; and ii. adding a first fluorescent moiety to hydryoxymethylcytosines in the sample, to label molecules that comprise hydroxymethylcytosine with the first fluorophore. This may be done in a single reaction or in consecutive reactions.

In the labeling step of the method, molecules that comprise hydroxymethylcytosine are labeled with a first fluorophore by incubating DNA molecules with a DNA D glucosyltransferase and UDP glucose modified with a chemoselective group, thereby covalently labeling the hydroxymethylated DNA molecules with the chemoselective group, and linking the first fluorophore to the chemoselectively-modified DNA via a cycloaddition reaction. In other words, the hydroxymethylated DNA molecules in the cIDNA are labeled with a with the chemoselective group, i.e., a group that can participate in a click reaction. This step may be done by incubating the adaptor-ligated cIDNA with DNA D-glucosyltransferase (e.g., T4 DNA D glucosyltransferase (which is commercially available from a number of vendors), although other DNA D-glucosyltransferases exist) and, e.g., UDP-6-N3-Glu (i.e., UDP glucose containing an azide). This step may be done using a protocol adapted from US20110301045 or Song et al, (Nat. Biotechnol. 2011 29: 68-72), for example. A first fluorophore can be added to the chemoselectively modified DNA via a cycloaddition (click) reaction. This step may be done by directly adding a fluorescent reactant, e.g., a dibenzocyclooctyne-modified fluorophore to the glucosyltransferase reaction after that reaction has been completed, i.e., after an appropriate amount of time (e.g., after 30 minutes or more). In some embodiments, the fluorescent reactant may be of the general formula F-X, where F is a fluorescent moiety and X is a group that reacts with the chemoselective group added to the cIDNA via a cycloaddition reaction. Cy3-DBCO and and Cy3-DBCO are examples of fluorescent reactants. In this step, the cycloaddition reaction may be between an azido group added to the hydroxymethylated cIDNA and an alkynyl group (e.g., dibenzocyclooctyne group) that is linked to the fluorophore. Again, this step may be done using a protocol adapted from US20110301045 or Song et al), Nat. Biotechnol. 2011 29: 68-72), for example.

The next step of the method comprises immobilizing the labeled DNA molecules on a support, e.g., a microscope slide. This step of the method may be done by using a slide that has been coated in a binding partner for the capture tag added to the DNA molecules. For example, in some embodiments, the labeled DNA molecules may be captured on a slide that is coated in neutravidin. These slides may be made by first passivating the slides in a mixture of polyethylene glycol (PEG) mPEG-SVA and biotin-PEG-SYA (at a ratio of, e.g., 99:1 (mol/mol)) to reduce non-specific binding of the DNA, and then coating the slide in neutravidin. The labeled DNA molecules can be immobilized on the surface of the slide, e.g., at a concentration of 10-300 pM (e.g., 30-100 pM) for a period of time, e.g., 5 minutes to 1 hour, e.g., 15 minutes.

Next, the method comprises imaging individual molecules of hydroxymethylated genomic DNA on the support at a single molecule resolution. This step may be done using any sensitive, high resolution, fluorescence detector. In some embodiment, the imaging may be done by total internal reflection fluorescence (TIRF) microscopy. This step of the method may produce one or more images of the labeled molecules on the support in which the molecules are spatially resolved. The image may show at least 1,000 (e.g., at least 5,000, at least 10,000, at least 20,000, at least 50,000, at least 100,000, up to 500,000 or more) spatially separated labeled molecules. As would be understood, the individual molecules are detected by detecting a light signal of a particular wavelength emanating from the first fluorophore added to those molecules.

After the labeled DNA molecules have been imaged, the method may comprise counting the number of individual molecules labeled with the first fluorophore, thereby determining the number of hydryoxymethylated DNA molecules in the sample.

In some embodiments, the initial labeling step may comprise adding a second fluorophore (i.e., a fluorophore that is distinguishable from the first fluorophore) to the ends of the DNA molecules in the sample. This may be done by, e.g., adding a mixture of a nucleotide that is linked to a capture tag and a fluorescent nucleotide to the terminal transferase reaction. In some embodiments, the nucleotide added in the terminal transferase reaction may be linked to both a capture agent and a fluorophore. In these embodiments, the imaging step may further comprise imaging individual molecules of methylated genomic DNA, at a single molecule resolution, by detecting a light signal emanating from the second fluorophore. As would be apparent, this embodiment of the method may further comprise counting: the number of individual molecules labeled with the first fluorophore and the number of individual molecules labeled with the second fluorophore. Labeling the ends of all of the DNA molecules with a second fluorophore provides a way to count the total number of DNA molecules in the sample. As such, adding a second fluorophore to the ends of the DNA molecules allows one to calculate the percentage of molecules in the sample that are hydroxymethylated.

In some embodiments, the labeling step may further comprise, after labeling the molecules that contain one or more hydroxymethylcytosine, labeling molecules that comprise methylcytosine with a second fluorophore. In these methods, the imaging step may further comprise imaging individual molecules of methylated genomic DNA on the support. As would be apparent, this embodiment may involve counting the number of individual molecules labeled with the first fluorophore and the number of individual molecules labeled with the second fluorophore. This embodiment of the method may further comprise calculating the relative amounts of hydroxymethylated DNA and methylated DNA in the sample. The molecules that comprise methylcytosine may be labeled with the second fluorophore by: incubating the product of the prior labeling reaction with a methylcytosine dioxygenase (e.g., TETI or the like), thereby enzymatically converting methylcytosine into hydroxymethylcytosine; incubating the methylcytosine dioxygenase-treated DNA with a DNA D-glucosyltransferase and UDP glucose modified with a chemoselective group to covalently label the hydroxymethylated DNA molecules with the chemoselective group, and linking the second fluorophore to the chemoselectively-modified DNA via a cycloaddition reaction. Except for the treatment with the methylcytosine dioxygenase, this reaction is similar to the reaction in which the first fluorophore is added to the DNA molecules.

In any embodiment in which a sample is labeled with two fluorophores (i.e., a first and second fluorophores), the fluorophores should be distinguishable, meaning that the molecules that are labeled with the different fluorophores can be independently detected and counted, even when the populations are mixed. Suitable distinguishable fluorescent label pairs useful in the subject methods include Cy-3 and Cy-5 (Amersham Inc., Piscataway, N.J.), Quasar 570 and Quasar 670 (Biosearch Technology, Novato Calif.), Alexafluor555 and Alexafluor647 (Molecular Probes, Eugene, Oreg.), BODIPY V-1002 and BODIPY V1005 (Molecular Probes, Eugene, Oreg.), POPO-3 and TOTO-3 (Molecular Probes, Eugene, Oreg.), and POPRO3 TOPRO3 (Molecular Probes, Eugene, Oreg.). Further suitable distinguishable detectable labels may be found in Kricka et al. (Ann Clin Biochem. 39:114-29, 2002). For example, the RCA products may be labeled with any combination of ATTO, ALEXA, CY, or dimeric cyanine dyes such as YOYO, TOTO etc.

As would be apparent, in imaging DNA molecules that have been labeled with at least two different fluorophores, appropriate filters should be used so that the signals from the first and second fluorophores can be separately detected and imaged.

In some embodiments, the proximity between a hydroxymethylcytosine and a methylcytosine may be determined by detecting a FRET (fluorescence resonance energy transfer) signal. In these embodiments, the labeling step of the method may further comprise: labeling molecules that comprise methylcytosine with a second fluorophore, as described above; and imaging individual molecules of genomic DNA by detecting a FRET signal emanating from the first or second fluorophores. A FRET signal indicates that a molecule has a hydroxymethylcytosine and a methylcytosine that are proximal to one another. In some cases, a FRET signal can be quantified to determine how proximal a hydroxymethylcytosine and a methylcytosine are, e.g., whether they are within 15-25 bases of one another, 5-14 bases of one another or 1-4 bases of one another. Depending on how the method is performed (e.g., depending on whether the labeled DNA molecules are denatured before they are immobilized on the substrate), the method can be used to determine whether a hydroxymethylcytosine and a methylcytosine are proximal on the same strand or on opposite strands.

The method described above may be generally applied to analyze biological DNA samples. For example, in some embodiments, the method in a method that involves: (a) quantifying, using the method described above: (i) the amount of hydroxymethylated DNA and, optionally, the amount of methylated DNA in a first sample and (i) the amount of hydroxymethylated DNA and, optionally, the amount of methylated DNA in second sample of cIDNA; and (b) comparing the results obtained in step (a) to determine if there is a difference in hydroxymethylation or methylation between the samples. In addition, the proximity between methylcytosines and hydroxymethylcytosines may be analyzed. At least one of the samples is a clinical sample, a sample containing DNA obtained from a patient.

In certain embodiments, two different DNA samples may be compared using the above methods. The different samples may be composed of an "experimental" sample, i.e., a DNA sample of interest, and a "control" DNA sample to which the experimental DNA sample may be compared. In many embodiments, the different samples are obtained from subjects, one subject being a subject of interest, e.g., patient with a disease, and the other a control subject, a patient does not have the disease. Exemplary sample pairs include, for example, DNA from a subject having a disease such as colon, breast, prostate, lung, skin cancer, or infected with a pathogen etc.) and cIDNA from normal subjects that do not have the disease, and cIDNA from two different time points from the same subject, e.g., before and after administration of a therapy, etc.

In some embodiment, the different samples may consist of an "experimental" sample, i.e., a sample of interest, and a "control" sample to which the experimental sample may be compared. In many embodiments, the different samples are pairs of cell types or fractions thereof, one cell type being a cell type of interest, e.g., an abnormal cell, and the other a control, e.g., normal, cell. If two fractions of cells are compared, the fractions are usually the same fraction from each of the two cells. In certain embodiments, however, two fractions of the same cell may be compared. Exemplary cell type pairs include, for example, cells isolated from a tissue biopsy (e.g., from a tissue having a disease such as colon, breast, prostate, lung, skin cancer, or infected with a pathogen etc.) and normal cells from the same tissue, usually from the same patient; cells grown in tissue culture that are immortal (e.g., cells with a proliferative mutation or an immortalizing transgene), infected with a pathogen, or treated (e.g., with environmental or chemical agents such as peptides, hormones, altered temperature, growth condition, physical stress, cellular transformation, etc.), and a normal cell (e.g., a cell that is otherwise identical to the experimental cell except that it is not immortal, infected, or treated, etc.); a cell isolated from a mammal with a cancer, a disease, a geriatric mammal, or a mammal exposed to a condition, and a cell from a mammal of the same species, preferably from the same family, that is healthy or young; and differentiated cells and non-differentiated cells from the same mammal (e.g., one cell being the progenitor of the other in a mammal, for example). In one embodiment, cells of different types, e.g., neuronal and non-neuronal cells, or cells of different status (e.g., before and after a stimulus on the cells) may be employed. In another embodiment of the invention, the experimental material is cells susceptible to infection by a pathogen such as a virus, e.g., human immunodeficiency virus (HIV), etc., and the control material is cells resistant to infection by the pathogen. In another embodiment of the invention, the sample pair is represented by undifferentiated cells, e.g., stem cells, and differentiated cells.

The methods described above may be used to identify a hydroxymethylation and/or methylation pattern that correlates with phenotype, e.g., a disease, condition or clinical outcome, etc. In some embodiments, this method may comprise (a) performing the above-described method on a plurality of DNA samples, wherein the DNA samples are isolated from patients having a known phenotype, e.g., disease, condition or clinical outcome, thereby determining a signature of hydroxymethylation and/or methylation in DNA from each of the patients; and (b) identifying a hydryoxymethylation signature that is correlated with the phenotype.

In some embodiments, the hydroxymethylation and/or methylation signature may be diagnostic (e.g., may provide a diagnosis of a disease or condition or the type or stage of a disease or condition, etc.), prognostic (e.g., indicating a clinical outcome, e.g., survival or death within a time frame) or theranostic (e.g., indicating which treatment would be the most effective).

Also provided is a method for analyzing a patient sample. In this embodiment, the method may comprise: (a) identifying, using the above-described method, a hydroxymethylation and/or methylation signature in the DNA of a patient; (b) comparing the identified sequences to a set of signatures that are correlated with a phenotype, e.g., a disease, condition, or clinical outcome etc.; and (c) providing a report indication a correlation with phenotype. This embodiment may further comprise making a diagnosis, prognosis or theranosis based on the results of the comparison.

Also provided is a method for labeling cell-free DNA (cIDNA). In some embodiments, this method may comprise: attaching labels to DNA molecules that comprise one or more hydroxymethylcytosine and methylcytosine nucleotides in a cIDNA sample, wherein the hydroxymethylcytosine nucleotides are labeled with a first label and the methylcytosine nucleotides are labeled with a second label that is different to the first label, to produce a labeled sample. This method may further comprise analyzing the labeled sample. In some embodiments, the first and second labels may distinguishable fluorophores, examples of which are described above. In some embodiments, the first and second labels may be different capture tags, thereby allowing the DNA molecules containing hydroxymethylcytosine nucleotides and the DNA containing methylcytosine nucleotides to be independently separated from the sample. In some cases, the molecules may contain an additional capture tag at an end.

Also provided is a method for analyzing genomic DNA molecules. In some embodiments this method may comprise: (a) labeling a sample comprising the genomic DNA by: (i) adding a capture tag to the ends of the DNA molecules, e.g., using a terminal transferase, as described above; and (ii) attaching labels to DNA molecules that comprise one or more hydroxymethylcytosine and methylcytosine nucleotides, wherein the hydroxymethylcytosine nucleotides are labeled with a first fluorophore and the methylcytosine nucleotides are labeled with a second fluorophore, wherein the first and second fluorophores are capable of generating a FRET signal (i.e., a fluorescence resonance energy transfer signal in which one of the fluorophores acts as a FRET donor and the other of the fluorophores acts as a FRET acceptor), to produce labeled genomic DNA; and (b) detecting a FRET signal from an individual molecule of the labeled genomic DNA (e.g., using fluorescence microscopy or another method. In these methods, the FRET signal is indicative of the proximity between one or more of the hydroxymethylcytosine and methylcytosine nucleotides in a molecule of the genomic DNA In some embodiments, the hydroxymethylcytosine nucleotides are labeled with a FRET donor and the methylcytosine nucleotides are labeled with FRET acceptor. In other embodiments the hydroxymethylcytosine nucleotides are labeled with a FRET acceptor and the methylcytosine nucleotides are labeled with FRET donor.

Also provided is a composition comprising genomic DNA, e.g., double-stranded DNA, wherein the hydroxymethylcytosine nucleotides are labeled with a first label, e.g., a first fluorophore and the methylcytosine nucleotides are labeled with a second label that is different to the first label, e.g., a second fluorophore In some embodiments, the method may involve creating a report as described above (an electronic form of which may have been forwarded from a remote location) and forwarding the report to a doctor or other medical professional to determine whether a patient has a phenotype (e.g., cancer, etc) or to identify a suitable therapy for the patient. The report may be used as a diagnostic to determine whether the subject has a disease or condition, e.g., a cancer. In certain embodiments, the method may be used to determine the stage or type cancer, to identify metastasized cells, or to monitor a patient's response to a treatment, for example.

In any embodiment, report can be forwarded to a "remote location", where "remote location," means a location other than the location at which the image is examined. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on web sites and the like. In certain embodiments, the report may be analyzed by an MD or other qualified medical professional, and a report based on the results of the analysis of the image may be forwarded to the patient from which the sample was obtained.

Also provided is a method for analyzing a sample comprising (a) determining, using the method described above, a hydroxymethylation and/or methylation signature in a first sample of DNA and a hydroxymethylation and/or methylation signature in a second sample of cIDNA, wherein the first and second samples of DNA are obtained from the same patient at two different time points; and (b) comparing the signatures to determine if there has been a change in hydroxymethylation and/or methylation over time. This method may be quantitative and, in some embodiments, the comparing step (b) may comprise comparing the level of hydroxymethylation and/or methylation over time. The comparison step of this method may map of the changes in hydroxymethylation and/or methylation in the course of a disease, condition, or a treatment of a disease or condition.

The phenotype of a patient can be any observable characteristic or trait of a subject, such as a disease or condition, a disease stage or condition stage, susceptibility to a disease or condition, prognosis of a disease stage or condition, a physiological state, or response to therapeutics, etc. A phenotype can result from a subject's gene expression as well as the influence of environmental factors and the interactions between the two, as well as from epigenetic modifications to nucleic acid sequences.

The phenotype in a subject can be characterized by analyzing DNA using the method described above. For example, characterizing a phenotype for a subject or individual may include detecting a disease or condition (including pre-symptomatic early stage detecting), determining the prognosis, diagnosis, or theranosis of a disease or condition, or determining the stage or progression of a disease or condition. Characterizing a phenotype can also include identifying appropriate treatments or treatment efficacy for specific diseases, conditions, disease stages and condition stages, predictions and likelihood analysis of disease progression, particularly disease recurrence, metastatic spread or disease relapse. A phenotype can also be a clinically distinct type or subtype of a condition or disease, such as a cancer or tumor. Phenotype determination can also be a determination of a physiological condition, or an assessment of organ distress or organ rejection, such as post-transplantation. The products and processes described herein allow assessment of a subject on an individual basis, which can provide benefits of more efficient and economical decisions in treatment.

In some embodiments, the method may be used to identify a signature that predicts whether a subject is likely to respond to a treatment for a disease or disorder.

Characterizing a phenotype may include predicting the responder/non-responder status of the subject, wherein a responder responds to a treatment for a disease and a non-responder does not respond to the treatment. If a hydroxymethylation and/or methylation signature in a subject more closely aligns with that of previous subjects that were known to respond to the treatment, the subject can be characterized, or predicted, as a responder to the treatment. Similarly, if the hydroxymethylation signature in the subject more closely aligns with that of previous subjects that did not respond to the treatment, the subject can be characterized, or predicted as a non responder to the treatment. The treatment can be for any appropriate disease, disorder or other condition. The method can be used in any disease setting where a hydroxymethylation signature that correlates with responder/non-responder status is known.

In some embodiments, the phenotype comprises a disease or condition such as those listed below. For example, the phenotype can comprise the presence of or likelihood of developing a tumor, neoplasm, or cancer. A cancer detected or assessed by products or processes described herein includes, but is not limited to, breast cancer, ovarian cancer, lung cancer, colon cancer, hyperplastic polyp, adenoma, colorectal cancer, high grade dysplasia, low grade dysplasia, prostatic hyperplasia, prostate cancer, melanoma, pancreatic cancer, brain cancer (such as a glioblastoma), hematological malignancy, hepatocellular carcinoma, cervical cancer, endometrial cancer, head and neck cancer, esophageal cancer, gastrointestinal stromal tumor (GIST), renal cell carcinoma (RCC) or gastric cancer. The colorectal cancer can be CRC Dukes B or Dukes C-D. The hematological malignancy can be B-Cell Chronic Lymphocytic Leukemia, B-Cell Lymphoma-DLBCL, B-Cell Lymphoma-DLBCL-germinal center-like, B-Cell Lymphoma-DLBCL-activated B-cell-like, and Burkitt's lymphoma.

In some embodiments, the phenotype may be a premalignant condition, such as actinic keratosis, atrophic gastritis, leukoplakia, erythroplasia, lymphomatoid granulomatosis, preleukemia, fibrosis, cervical dysplasia, uterine cervical dysplasia, xeroderma pigmentosum, Barrett's Esophagus, colorectal polyp, or other abnormal tissue growth or lesion that is likely to develop into a malignant tumor. Transformative viral infections such as HIV and HPV also present phenotypes that can be assessed according to the method.

The cancer characterized by the present method may be, without limitation, a carcinoma, a sarcoma, a lymphoma or leukemia, a germ cell tumor, a blastoma, or other cancers. Carcinomas include without limitation epithelial neoplasms, squamous cell neoplasms squamous cell carcinoma, basal cell neoplasms basal cell carcinoma, transitional cell papillomas and carcinomas, adenomas and adenocarcinomas (glands), adenoma, adenocarcinoma, linitis plastica insulinoma, glucagonoma, gastrinoma, vipoma, cholangiocarcinoma, hepatocellular carcinoma, adenoid cystic carcinoma, carcinoid tumor of appendix, prolactinoma, oncocytoma, hurthle cell adenoma, renal cell carcinoma, grawitz tumor, multiple endocrine adenomas, endometrioid adenoma, adnexal and skin appendage neoplasms, mucoepidermoid neoplasms, cystic, mucinous and serous neoplasms, cystadenoma, pseudomyxoma peritonei, ductal, lobular and medullary neoplasms, acinar cell neoplasms, complex epithelial neoplasms, warthin's tumor, thymoma, specialized gonadal neoplasms, sex cord stromal tumor, thecoma, granulosa cell tumor, arrhenoblastoma, sertoli leydig cell tumor, glomus tumors, paraganglioma, pheochromocytoma, glomus tumor, nevi and melanomas, melanocytic nevus, malignant melanoma, melanoma, nodular melanoma, dysplastic nevus, lentigo maligna melanoma, superficial spreading melanoma, and malignant acral lentiginous melanoma. Sarcoma includes without limitation Askin's tumor, botryodies, chondrosarcoma, Ewing's sarcoma, malignant hemangio endothelioma, malignant schwannoma, osteosarcoma, soft tissue sarcomas including: alveolar soft part sarcoma, angiosarcoma, cystosarcoma phyllodes, dermatofibrosarcoma, desmoid tumor, desmoplastic small round cell tumor, epithelioid sarcoma, extraskeletal chondrosarcoma, extraskeletal osteosarcoma, fibrosarcoma, hemangiopericytoma, hemangiosarcoma, kaposi's sarcoma, leiomyosarcoma, liposarcoma, lymphangiosarcoma, lymphosarcoma, malignant fibrous histiocytoma, neurofibrosarcoma, rhabdomyosarcoma, and synovial sarcoma. Lymphoma and leukemia include without limitation chronic lymphocytic leukemia/small lymphocytic lymphoma, B-cell prolymphocytic leukemia, lymphoplasmacytic lymphoma (such as waldenstrom macroglobulinemia), splenic marginal zone lymphoma, plasma cell myeloma, plasmacytoma, monoclonal immunoglobulin deposition diseases, heavy chain diseases, extranodal marginal zone B cell lymphoma, also called malt lymphoma, nodal marginal zone B cell lymphoma (nmzl), follicular lymphoma, mantle cell lymphoma, diffuse large B cell lymphoma, mediastinal (thymic) large B cell lymphoma, intravascular large B cell lymphoma, primary effusion lymphoma, burkitt lymphoma/leukemia, T cell prolymphocytic leukemia, T cell large granular lymphocytic leukemia, aggressive NK cell leukemia, adult T cell leukemia/lymphoma, extranodal NK/T cell lymphoma, nasal type, enteropathy-type T cell lymphoma, hepatosplenic T cell lymphoma, blastic NK cell lymphoma, mycosis fungoides/sezary syndrome, primary cutaneous CD30-positive T cell lymphoproliferative disorders, primary cutaneous anaplastic large cell lymphoma, lymphomatoid papulosis, angioimmunoblastic T cell lymphoma, peripheral T cell lymphoma, unspecified, anaplastic large cell lymphoma, classical hodgkin lymphomas (nodular sclerosis, mixed cellularity, lymphocyte rich, lymphocyte depleted or not depleted), and nodular lymphocyte-predominant hodgkin lymphoma. Germ cell tumors include without limitation germinoma, dysgerminoma, seminoma, nongerminomatous germ cell tumor, embryonal carcinoma, endodermal sinus tumor, choriocarcinoma, teratoma, polyembryoma, and gonadoblastoma. Blastoma includes without limitation nephroblastoma, medulloblastoma, and retinoblastoma. Other cancers include without limitation labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma.

In a further embodiment, the cancer under analysis may be a lung cancer including non small cell lung cancer and small cell lung cancer (including small cell carcinoma (oat cell cancer), mixed small cell/large cell carcinoma, and combined small cell carcinoma), colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemia, lymphoma, myeloma, or a solid tumor.

In further embodiments, the cancer may be an acute lymphoblastic leukemia; acute myeloid leukemia; adrenocortical carcinoma; AIDS-related cancers; AIDS-related lymphoma; anal cancer; appendix cancer; astrocytomas; atypical teratoid/rhabdoid tumor; basal cell carcinoma; bladder cancer; brain stem glioma; brain tumor (including brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma); breast cancer; bronchial tumors; Burkitt lymphoma; cancer of unknown primary site; carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonary blastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sezary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymic carcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenstrom macroglobulinemia; or Wilm's tumor. The methods of the invention can be used to characterize these and other cancers. Thus, characterizing a phenotype can be providing a diagnosis, prognosis or theranosis of one of the cancers disclosed herein.

The phenotype can also be an inflammatory disease, immune disease, or autoimmune disease. For example, the disease may be inflammatory bowel disease (IBD), Crohn's disease (CD), ulcerative colitis (UC), pelvic inflammation, vasculitis, psoriasis, diabetes, autoimmune hepatitis, Multiple Sclerosis, Myasthenia Gravis, Type I diabetes, Rheumatoid Arthritis, Psoriasis, Systemic Lupus Erythematosis (SLE), Hashimoto's Thyroiditis, Grave's disease, Ankylosing Spondylitis Sjogrens Disease, CREST syndrome, Scleroderma, Rheumatic Disease, organ rejection, Primary Sclerosing Cholangitis, or sepsis.

The phenotype can also comprise a cardiovascular disease, such as atherosclerosis, congestive heart failure, vulnerable plaque, stroke, or ischemia. The cardiovascular disease or condition can be high blood pressure, stenosis, vessel occlusion or a thrombotic event.

The phenotype can also comprise a neurological disease, such as Multiple Sclerosis (MS), Parkinson's Disease (PD), Alzheimer's Disease (AD), schizophrenia, bipolar disorder, depression, autism, Prion Disease, Pick's disease, dementia, Huntington disease (HD), Down's syndrome, cerebrovascular disease, Rasmussen's encephalitis, viral meningitis, neurospsychiatric systemic lupus erythematosus (NPSLE), amyotrophic lateral sclerosis, Creutzfeldt-Jacob disease, Gerstmann-Straussler-Scheinker disease, transmissible spongiform encephalopathy, ischemic reperfusion damage (e.g. stroke), brain trauma, microbial infection, or chronic fatigue syndrome. The phenotype may also be a condition such as fibromyalgia, chronic neuropathic pain, or peripheral neuropathic pain.

The phenotype may also comprise an infectious disease, such as a bacterial, viral or yeast infection. For example, the disease or condition may be Whipple's Disease, Prion Disease, cirrhosis, methicillin-resistant *Staphylococcus aureus*, HIV, hepatitis, syphilis, meningitis, malaria, tuberculosis, or influenza. Viral proteins, such as HIV or HCV-like particles can be assessed in a vesicle, to characterize a viral condition.

The phenotype can also comprise a perinatal or pregnancy related condition (e.g. preeclampsia or preterm birth), metabolic disease or condition, such as a metabolic disease or condition associated with iron metabolism. For example, hepcidin can be assayed in a vesicle to characterize an iron deficiency. The metabolic disease or condition can also be diabetes, inflammation, or a perinatal condition.

The DNA used in the method may be from a mammal such as bovine, avian, canine, equine, feline, ovine, porcine, or primate animals (including humans and non-human primates). In some embodiments, the subject can have a pre-existing disease or condition, such as cancer. Alternatively, the subject may not have any known pre-existing condition. The subject may also be non-responsive to an existing or past treatment, such as a treatment for cancer. In some embodiments, the cfDNA may be from a pregnant female. In some embodiments, the hydroxymethylation pattern in the fetal fraction of the cIDNA may correlate with a chromosomal abnormality in the fetus (e.g., an aneuploidy). In other embodiments, one can determine the sex of the fetus from the hydroxymethylation pattern in the fetal fraction of the cIDNA and/or determine the fetal fraction of the cIDNA.

Kits

Also provided by this disclosure are kits that contain reagents for practicing the subject methods, as described above. The subject kits contain one or more of any of the components described above.

The various components of the kit may be present in separate containers or certain compatible components may be precombined into a single container, as desired.

In addition to above-mentioned components, the subject kits may further include instructions for using the components of the kit to practice the subject methods, i.e., instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc.

In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

Aspects of the present teachings can be further understood in light of the following examples, which should not be construed as limiting the scope of the present teachings in any way.

Materials and Methods

Preparation of genomic DNA Mouse tissue genomic DNA was extracted using Wizard Genomic DNA Purification Kit (Promega) following the manufacture's recommendation. Genomic DNA was digested with dsDNA Fragmentase (NEB) to 50-200 bp following the manufacture's recommendation and analyzed by agarose gel electrophoresis to determine the average fragment length.

Preparation of synthetic DNA Oligonucleotides containing 5mC, 5hmC, biotin, Cy3, Cy5, FAM are ordered from Integrated DNA Technologies. Equal molar of two complementary strands are slow annealed to form duplex DNA Sequences of synthetic DNA are as follows:

5hmC_5mC_22 bp, X = 5mC, Y = 5hmC:
(SEQ IDNO: 1)
5' CCCGAXGCATGATCTGTACTTGATCGACYGTGCAAC 3'

(SEQ IDNO: 2)
3' GGGCTGCGTACTAGACATGAACTAGCTGGCACGTTG-biotin 5'

5hmC_5mC_9 bp, X = 5mC, Y = 5hmC:
(SEQ ID NO: 3)
5' CCCGACGCATGATCTGTAXTTGATCGACYGTGCAAC 3'

(SEQ IDNO: 4)
3' GGGCTGCGTACTAGACATGAACTAGCTGGCACGTTG-biotin 5'

5hmC_5mC_1 bp, X = 5mC, Y = 5hmC:
(SEQ IDNO: 5)
5' CCCGAXGYATGATCTGTACTTGATCGACCGTGCAAC 3'

(SEQ IDNO: 6)
3' GGGCTGCGTACTAGACATGAACTAGCTGGCACGTTG-biotin 5'

5hmC/5mC_CpG, X, Y = 5mC or 5hmC:
(SEQ IDNO: 7)
5' TCGATGTAGTGCGTCACYGGATGATAGCTGTACTCA 3'

(SEQ IDNO: 8)
3' AGCTACATCACGCAGTGGXCTACTATCGACATGAGT-biotin 5'

5hmC/5mC_CpG_FAM, X = 5mC, Y = 5mC or 5hmC:
(SEQ IDNO: 9)
5' TCGATGTAGTGCGTCACYGGATGATAGCTGTACTCA 3'

(SEQ IDNO: 10)
3' AGCTACATCACGCAGTGGXCTACTATCGACATGAGT-FAM 5'

End-labeling of genomic DNA fragments with biotin and Cy3. To end-label genomic DNA fragment with biotin and Cy3, 50 ng genomic DNA fragment was incubated in a 10 µL solution containing IX Terminal Transferase Reaction Buffer (NEB), 0.25 mM CoC12, 50 µM biotin-16-Aminoallyl-2'-dCTP (Trilink), 50 µM Cy3-dCTP (GE Healthcare), and 10 U Terminal Transferase (NEB) for 0.5 hat 37 DC. To end-label genomic DNA fragment with biotin only, 50 ng genomic DNA fragment was incubated with Terminal Transferase as described in the presence of 250 µM biotin-16-Aminoallyl-2'-dCTP. The end-labeled DNA was purified by DNA Clean & Concentrator-5 (Zymo) following the manufacturer's recommendation and eluted in 8 µLH2O.

Single-labeling of 5hmC with Cy5. Biotin and Cy3 end-labeled DNA was incubated in a 10 µL solution containing 50 mM HEPES buffer (pH 8), 25 mM MgCl2, 75 µM UDP-6-N3-Glc (Active Motif), and I U GT (5-hmC glucosyltransferase, Zymo) for I hat 37 DC. Then 2.5 µL Cy5 DBCO (10 mM stock in DMSO, Click Chemistry Tools) was directly added to the reaction mixture and incubated overnight at 37° C. The 5hmC-labeled DNA was purified by DNA Clean & Concentrator-5 (Zymo) following the manufacturer's recommendation and eluted in EB buffer (Qiagen). DNA concentration was determined by Qubit Fluorometer (Life Technologies).

Dual-labeling of 5hmC and 5mC with Cy5 and Cy3. 5hmC labeling and biotin end labeling of DNA was performed as described above and the 5hmC-labeled DNA was purified into 8 µL H2O. Next, Tetl oxidation was carried out by incubating the 5hmC-labeled DNA in a 10 µL solution containing 50 mM HEPES buffer (pH 8), 10 mM MgCl2, 75 mM ammonium iron (II) sulfate, 2 mM ascorbic acid, 1 mM a-ketoglutarate, 90 µM UDP-6-N3-Glc, 1 mM dithiothreitol, 2 U GT, and 2 µM Tetl (Wisegene) for 1 hat 37 DC. The DNA was purified and incubated with 2 mM Cy3 DBCO (Click Chemistry Tools) overnight at 37 DC in presence of 50 mM HEPES buffer (pH 8), 10 mM MgCl2. The dual-labeled DNA was purified by DNA Clean & Concentrator-5 into EB buffer. DNA concentration was determined by Qubit Fluorometer.

Dual-labeling of 5hmC and 5mC with Cy3 and Cy5 for smFRET. The biotin end-labeled DNA was incubated in a 10 µL solution containing 50 mM HEPES buffer (pH 8), 25 mM MgCl2, 150 μM UDP-6-N3-Glc (Active Motif), and 1 U GT for 1 h at 37 DC. Then 1 U fresh GT and 200 μM unmodified UDP-Glc (NEB) was added to the reaction and incubated for 1 h at 37 DC. The DNA was purified and incubated with 2 mM Cy3 DBCO (Click Chemistry Tools) overnight at 37 DC in presence of 50 mM HEPES buffer (pH 8), 10 mM MgCl2. The 5hmC labeled DNA was purified and oxidized with Tet1 and labelled with Cy5 DBCO as described above. The dual-labeled DNA was purified by DNA Clean & Concentrator-5 into EB buffer.

DNA Concentration was Determined by Qubit Fluorometer.

Denaturing dual-labeled sample for smFRET. Dual-labeled synthetic DNA was first end labeled with biotin as described above. 50 μL 50 pM dual-labeled synthetic DNA or genomic DNA samples in EB buffer were heated for 10 min at 100 DC and immediately put on ice for 10 min before smFRET experiments.

Single-molecule imaging through Total Internal Reflection Fluorescence (TIRF) Microscope. A quartz slide was first coated with polyethylene glycol (PEG) molecules (99:1 (mol/mol) mPEG-SVA:biotin-PEG-SVA (Laysan Bio)) to eliminate non-specific binding of DNA (Joo C, et al. (2006) Real-time observation of RecA filament dynamics with single monomer resolution. Cell 126(3):515-527). The slide was then assembled into a flow chamber and coated with neutravidin by flowing in 0.2 mg/ml solution. Through the specific interaction between biotin and neutravidin, the dye-labeled DNAs conjugated with biotin were immobilized on the PEG-coated surface by an incubation at a concentration of 30-100 pM for 15 minutes. After washing out the free DNAs, the FRET measurements by a total internal reflection fluorescence (TIRF) microscope were performed with an oxygen scavenger system (0.1 mg/ml glucose oxidase and 0.02 mg/ml catalase) and Trolox to eliminate single-molecule blinking events (Rasnik I, McKinney S A, Ha T (2006) Nonblinking and long-lasting single-molecule fluorescence imaging. Nat. Methods 3(11):891-893). Details of the wide-field TIRF microscope have been reported (30). Briefly, the excitation beam was focused into a pellin broca prism (CVI Laser), which was placed on top of a quartz slide with a thin layer of immersion oil in between to match the index of refraction. Cy3 (donor) and Cy5 (acceptor) dyes were excited through the dual-laser excitation system (532 nm and 633 nm) via TIRF. The fluorescence signals from Cy3 and Cy5 that were collected by a water immersion objective lens (60×, 1.2 N.A. Nikon) went through a notch filter to block out excitation beams. The emission signals of Cy5 dyes were separated by a 630 nm dichroic mirror (630DCXR, Chroma Technology) and detected by the electron-multiplying charge-coupled device camera (iXon 897, Andor Technology) with a time resolution of 100 ms. The fluorescence signal, recorded in real time by using software written in Visual C++ (Microsoft), was amplified before camera readout, which produced an arbitrary unit for the recorded fluorescence intensity. The single-molecule data analysis was carried out by programs written in Visual C++ (Microsoft). The FRET efficiency, E, was calculated as the intensity of the acceptor channel divided by the total intensity, which is the sum of donor and acceptor channel intensities.

Electrophoretic mobility shift assay. The MBD domain of MBD2 (from MethylMiner Methylated DNA Enrichment Kit, Life Technologies) at varying concentrations was incubated with 10 nM 36_5hmC/5mC_CpG FAM duplex DNA, 50 ng/μl of poly(dA-dT)/poly(dA-dT) (Sigma) in 20 mM HEPES (pH 8), 1 mM EDTA, 0.05% Triton X-100, and 30 mM KCl for 15 min at room temperature in a 10 μL reaction volume, prior to the addition of 2.5 μL Hi-Density TBE Sample Buffer (Life Technologies). The binding reactions were then loaded onto 6% DNA retardation gel (Life Technologies) and visualized with a Typhoon 9410 imager by using standard Blue FAM filter set (Aex=488 nm, Aem=520 nm).

Results

5-Methylcytosine (5mC) and 5-hydroxymethylcytosine (5hmC) are the two major DNA epigenetic modifications in mammalian genomes and play crucial roles in development and pathogenesis. Little is known about the co-localization or potential correlation of these two modifications. Presented herein is an ultra-sensitive single-molecule imaging technology capable of detecting and quantifying 5hmC and 5mC from trace amounts of DNA. This approach was used to perform single-molecule fluorescence resonance energy transfer (smFRET) experiments which measure the proximity between 5mC and 5hmC in the same DNA molecule. The results reveal high levels of adjacent and opposing methylated and hydroxymethylated CpG sites (5hmC/5mCpGs) in mouse genomic DNA across multiple tissues. The results identify the previously undetectable and unappreciated 5hmC/5mCpGs as one of the major states for 5hmC in the mammalian genome and suggest that they could function in promoting gene expression.

Figure 1B:
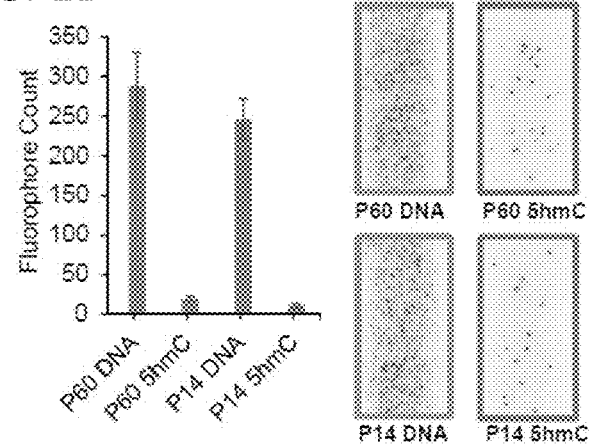
Figure 1C:
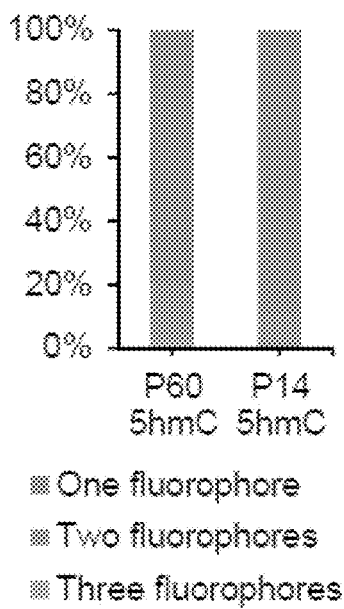
Figure 1D:
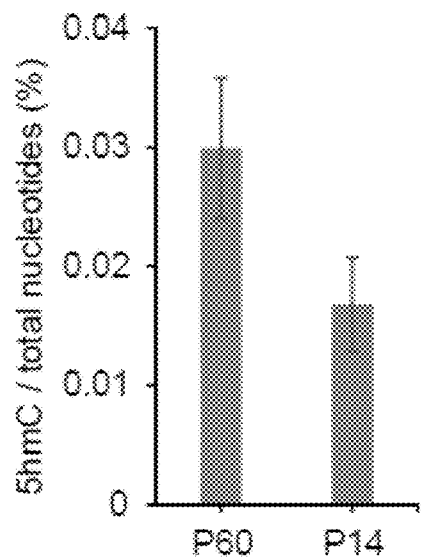
Figure 5:
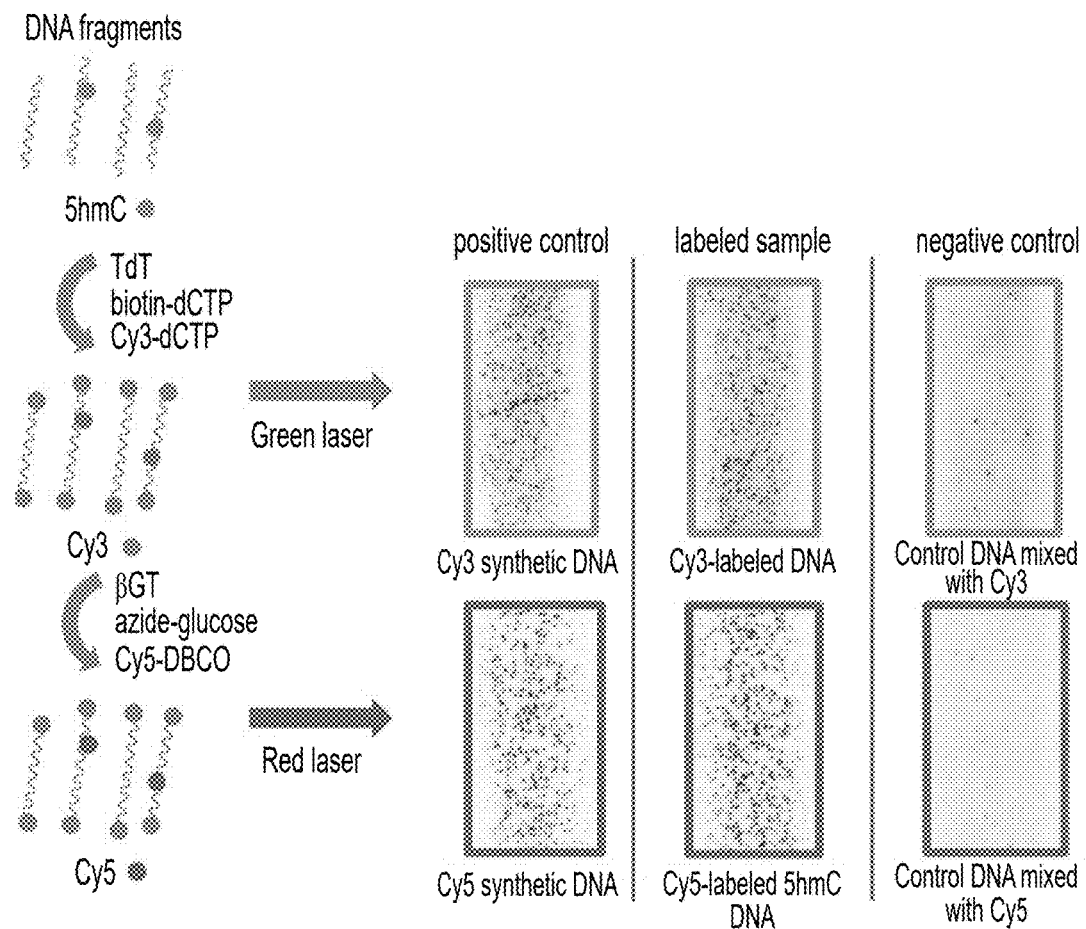
FIG. 5. Example images of step-wise labeling reaction using model DNA Positive controls are synthetic DNA bearing biotin and fluorophore. Top row labeled sample is biotin and Cy3 end-labeled genomic DNA fragments. Bottom row labeled sample is synthetic DNA bearing 5hmC and biotin after labeling reaction. Negative controls are synthetic DNA bearing biotin incubated with fluorophore without the enzymes. All DNA concentrations are 30 pM.
Figure 6:
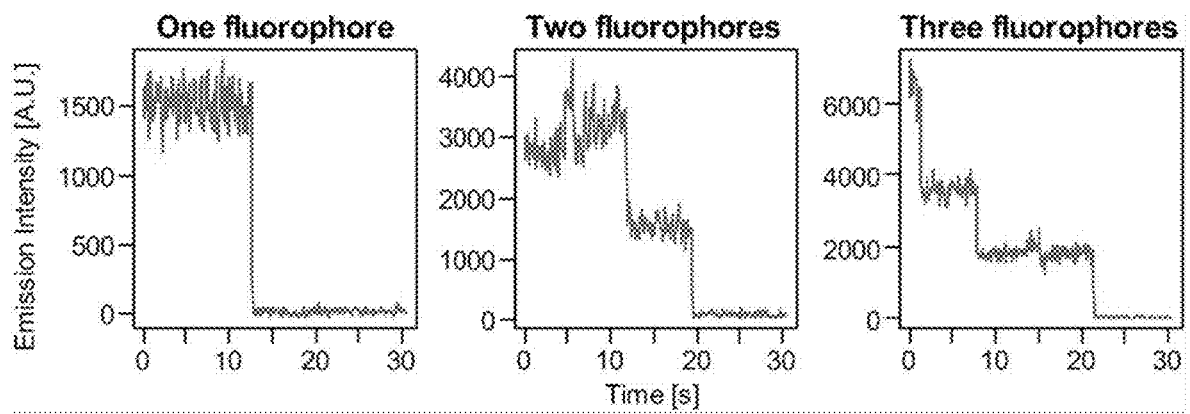
FIG. 6. Example photobleaching traces of single and multiple fluorophores.

This imaging approach uses a selective chemical labeling strategy (Song C X, et al. (2011) Selective chemical labeling reveals the genome-wide distribution of 5-hydroxymethylcytosine. Nat. Biotechnol. 29(1):68-72) to label DNA base modifications with specific fluorophores, followed by single-molecule imaging fluorescent assays (Jain A, et al. (2011) Probing cellular protein complexes using single-molecule pull-down. Nature 473(7348):484-U322) (FIG. IA and FIG. 5). This method is highly modular and can be used to image just one modification or multiple modifications simultaneously. To image 5hmC, the DNA fragments are first end-labeled with biotin and Cy3 by using Terminal Transferase (TdT) and modified dCTP. The biotin is used to immobilize DNA molecules to the microscope slide and the Cy3 serves as a counter for total amount of DNA. Next— glucosytransferase (GT) is used to label 5hmC with Cy5 via an azide-modified glucose. The dye-labeled biotinylated DNA is then captured by surface-tethered neutravidin on a passivated microscope slide and imaged with single-molecule total internal reflection fluorescence (TIRF) microscopy (FIG. 1A and FIG. 5). The number of 5hmC containing molecules and total amount of DNA can be determined by counting the fluorophores in the red channel (Cy5) and green channel (Cy3), respectively. Using synthetic DNA constructs we confirmed that the step-wise labeling is highly efficient and shows minimum background (FIG. 5). The method was applied to postnatal day 60 (P60) and postnatal day 14 (P14) mouse cerebellum genomic DNA (FIG. 1B). In addition to counting the fluorophores by direct emission, we also used photobleaching to detect multiple fluorophores in individual DNA molecules (FIG. 1C and FIG. 6). The 5hmC level can then be calculated based on the fluorophore counts, multiple fluorophore correction and the average length of the DNA fragments (FIG. 1D). The results are comparable to what has been found in bulk samples by previous HPLC-MS techniques (Globisch D, et al. (2010) Tissue distribution of 5-hydroxymethylcytosine and search for active demethylation intermediates. PLoS One 5(12):e15367) and also reveal the age-dependent increase of 5hmC in mouse cerebellum from P14 to P60 as previously reported (Song C X, et al. (2011) Selective chemical labeling reveals the genome-wide distribution of 5-hydroxymethylcytosine. Nat. Biotechnol. 29(1):68-72).

Figure 2A:
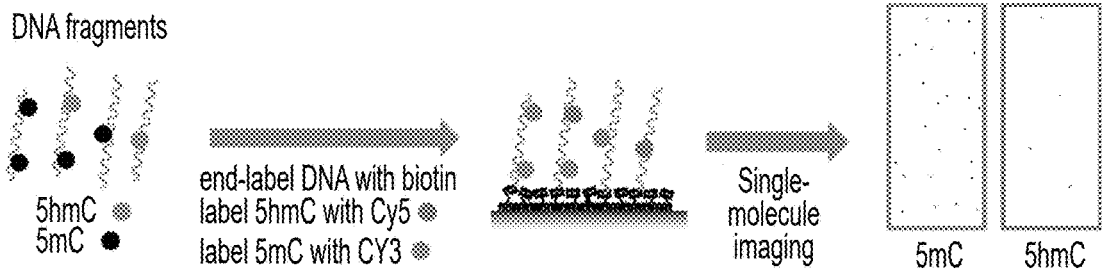
FIG. 2A. Dual-labeling of 5mC and 5hmC for simultaneous imaging. General procedure for dual-labeling and simultaneous imaging of 5mC and 5hmC. DNA fragments are end-labeled with biotin, 5hmC is labeled with Cy5 and 5mC is labeled with Cy3. The labeled DNA is immobilized to the microscope slide and imaged with single-molecule TIRF microscopy.
Figure 2B:
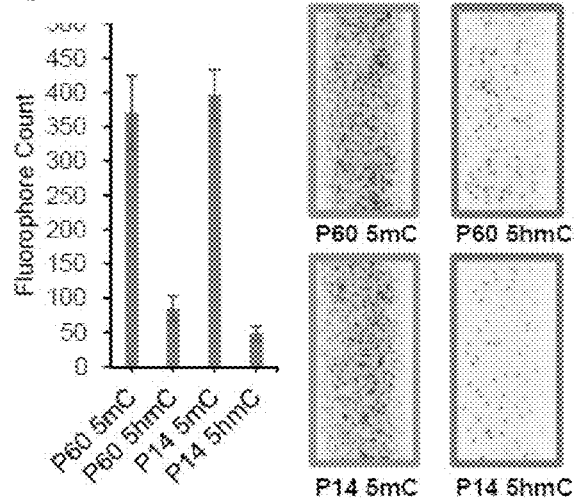
FIG. 2B. Dual-labeling of 5mC and 5hmC for simultaneous imaging. Fluorophore counts of dual-labeled P60 and P14 mouse cerebellum genomic DNA with example images shown on the right.
Figure 2C:
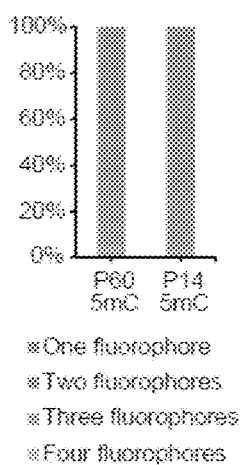
FIG. 2C. Dual-labeling of 5mC and 5hmC for simultaneous imaging. Distribution of multiple fluorophores on DNA fragment of mouse cerebellum when detecting 5mC.
Figure 2D:
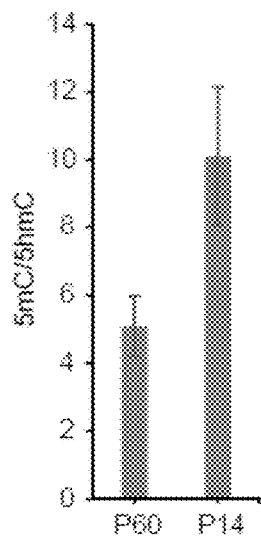
FIG. 2D. Dual-labeling of 5mC and 5hmC for simultaneous imaging. 5mC to 5hmC ratio in mouse cerebellum genomic DNA after adjusting multiple fluorophores.
Figure 2E:
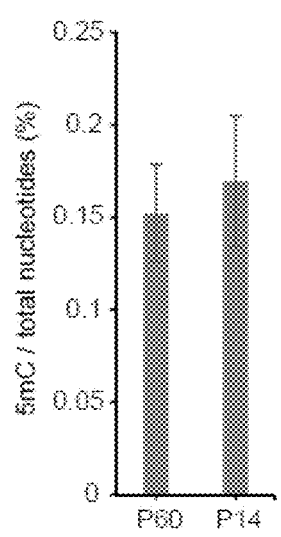
FIG. 2E. Dual-labeling of 5mC and 5hmC for simultaneous imaging. 5mC level of mouse cerebellum DNA Error bars, mean±SD (n=15 counting regions).
Figure 7:
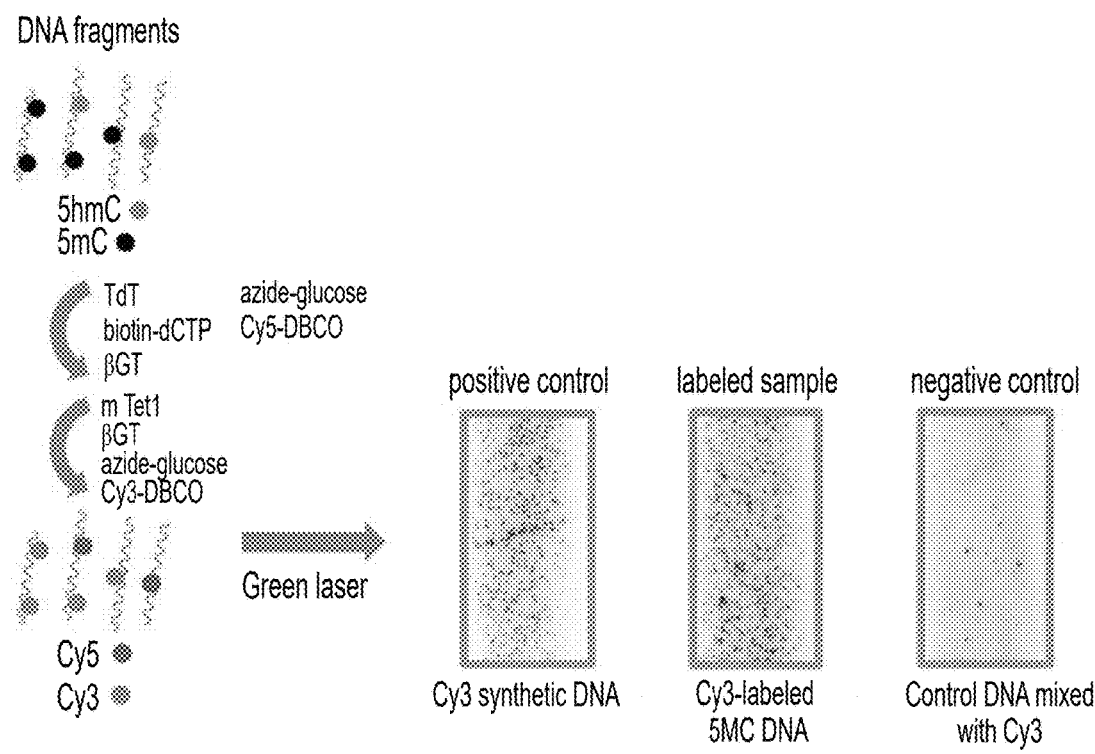
FIG. 7. Example images of 5mC labeling using model DNA Positive control is synthetic DNA bearing biotin and fluorophore. Labeled samples is synthetic DNA bearing 5mC and biotin after labeling reaction. Negative controls are synthetic DNA bearing biotin incubated with fluorophore without the enzymes. All synthetic DNA concentrations are 30 pM.
Figure 8:
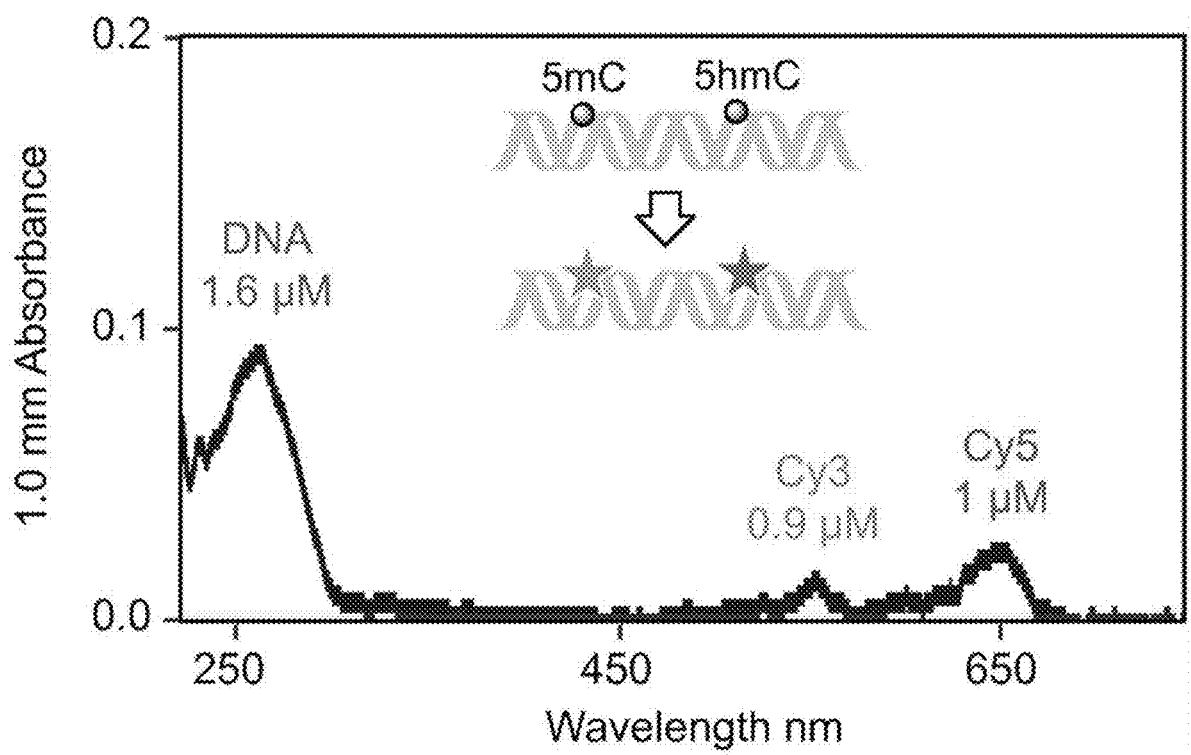
FIG. 8. An absorbance spectrum of a 36mer synthetic DNA bearing one 5mC and one 5hmC after the dual labeling reaction in which 5mC is labeled with Cy3 and 5hmC is labeled with Cy5. The absorption peaks at 260 nm, 555 nm and 647 nm correspond to the absorption maxima of DNA, Cy3, and Cy5 respectively. The concentrations are calculated using the extinction coefficients of the synthetic DNA, Cy3 and Cy5.

To image 5mC and 5hmC simultaneously, a dual-labeling strategy was developed (FIG. 2A and FIG. 7). DNA fragments were first end-labeled with biotin and labeled 5hmC with Cy5 as described above. Then GT and Tet1 was employed in a one-pot procedure to label 5mC with Cy3 (Zhang L, et al. (2013) Tet-mediated covalent labelling of 5-methylcytosine for its genome wide detection and sequencing. Nat. Commun. 4:1517) (FIG. 2A and FIG. 7). The number of 5hmC and 5mC modifications can be determined by counting the fluorophores in the red channel (Cy5) and green channel (Cy3), respectively. The 5mC labeling was highly efficient as indicated by experiments with synthetic DNA (FIG. 7). The labeling efficiencies of both 5hmC and 5mC are about 60% as estimated by the absorption spectrum of the dual-labeled DNA (FIG. 8). The dual-labeling strategy was also validated on mouse cerebellum genomic DNA By counting Cy3 on 5mC and Cy5 on 5hmC we obtained the ratio between 5mC and 5hmC occurrence (FIG. 2B). As expected, in addition to higher counts of 5mC than that of 5hmC, we observed more multiple fluorophores events on 5mC than on 5hmC (FIG. 2C), which was factored into the final 5mC to 5hmC ratio (FIG. 2D). We calculated the absolute 5mC level from the previous 5hmC measurement (FIG. 2E). Unlike 5hmC, the 5mC level did not change significantly between P14 and P60.

Thanks to the ultra-high sensitivity of single-molecule imaging, this method only requires 50 picograms of DNA or less for each measurement, representing orders of magnitude less DNA than is required by previous quantification methods such as the HPLC-MS or other fluorescence based methods (Globisch D, et al. (2010) Tissue distribution of 5-hydroxymethylcytosine and search for active demethylation intermediates. PLoS One 5(12):e15367; Michaeli Y, et al. (2013) Optical detection of epigenetic marks: sensitive quantification and direct imaging of individual hydroxymethylcytosine bases. Chem. Commun. (Camb.) 49(77):8599-8601; Shahal T, et al. (2014) Spectroscopic quantification of 5-hydroxymethylcytosine in genomic DNA. Anal. Chem. 86(16):8231-8237 and Nifker G, et al. (2015) One-Pot Chemoenzymatic Cascade for Labeling of the Epigenetic Marker 5-Hydroxymethylcytosine. Chem BioChem. 21-23). Besides being a general detection and quantification method, single-molecule imaging provides a unique opportunity to study the co-localization states of 5mC and 5hmC, which has been unknown since no previous method could perform an integrated analysis of 5mC and 5hmC in the same DNA molecule. With the dual-labeling scheme described above, one can for the first time measure the proximity between 5mC and 5hmC in the same DNA molecule.

Since 5mC is much more abundant than 5hmC, we switched the fluorescence labels on the modification for the smFRET experiment so that there are more acceptors (5mC-Cy5) than donors (5hmC-Cy3) (FIG. 3A). Synthetic DNA with 5hmC and 5mC separated by defined distances was used for smFRET measurement. Low FRET (~0.1), middle-FRET (~0.6), and high-FRET (~0.82) states were observed when 5hmC and 5mC are 22 bp, 9 bp, and 1 bp apart, respectively (FIG. 3B). A synthetic DNA was constructed with adjacent and opposing hemi hydroxymethylated/hemi-methylated CpG sites (5hmC/5mCpGs) and observed a high-FRET (~0.78) state (FIG. 3C). Surprisingly, when smFRET measurement were performed on mouse cerebellum DNA, it was observed that a distinct high-FRET peak (~0.78) with no middle-FRET peaks in between in both P60 and P14 samples (FIG. 3D). To determine whether this high FRET state was from 5hmC and 5mC on the same strand or from 5hmC and 5mC on the CpG site, the DNA was denatured before smFRET experiment. As expected, synthetic DNA with 5hmC and 5mC on the same strand retained the FRET signal whereas synthetic DNA with 5hmC/5mCpGs lost the FRET signal after denaturing (FIG. 9A-B). Both P60 and P14 mouse cerebellum DNA lost the FRET signal after denaturing, confirming the high FRET state was from adjacent and opposing CpG sites (FIG. 9C-D).

Figure 11:
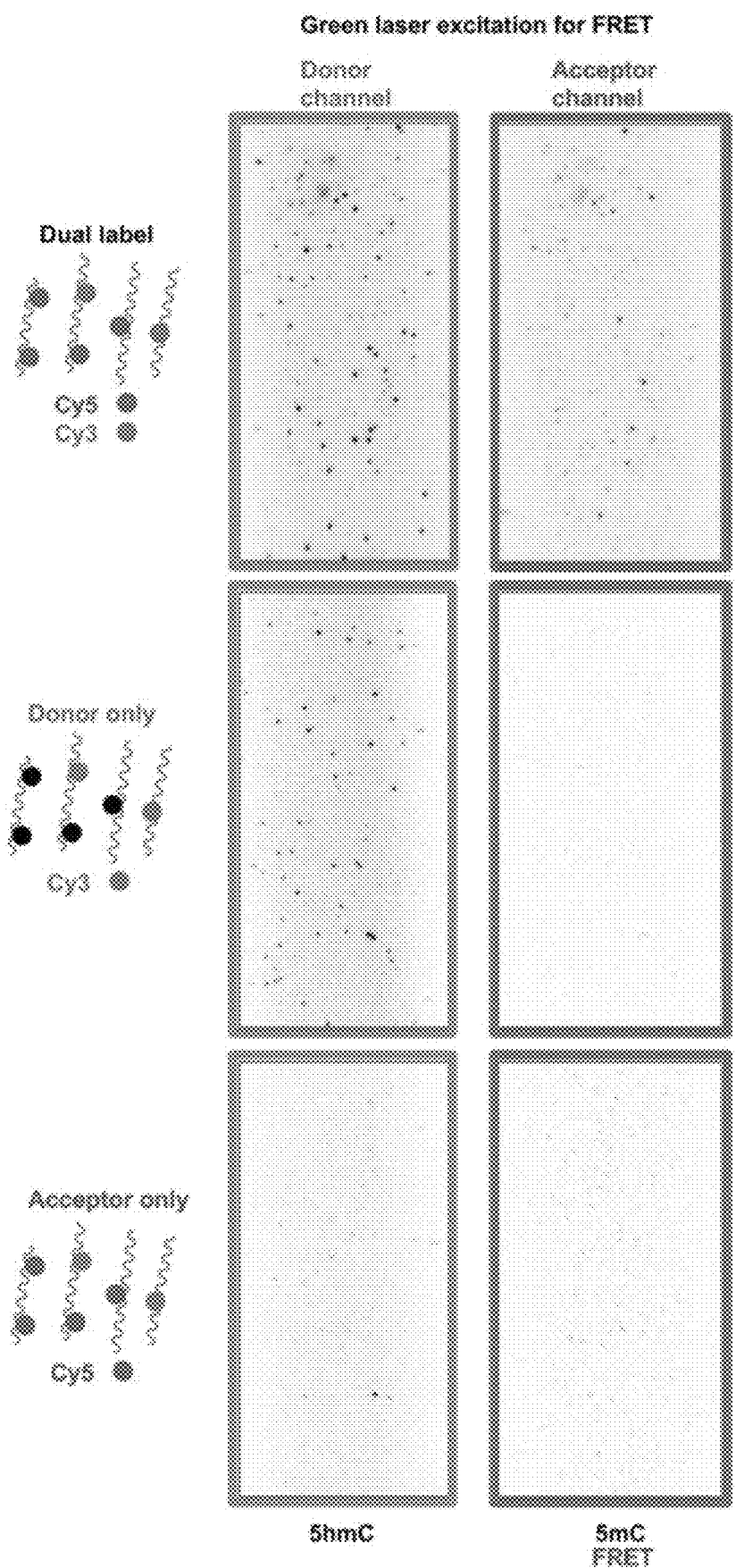
FIG. 11. Example images of smFRET experiment of P60 mouse cerebellum DNA Top row: example image of the dual labeled DNA Middle row: example image of the donor-only labeled DNA Bottom row: example image of the acceptor-only labeled DNA FIG. 12. Example anticorrelation traces of smFRET experiment of P60 mouse cerebellum DNA Arrows indicate anticorrelated intensity changes.
Figure 12:
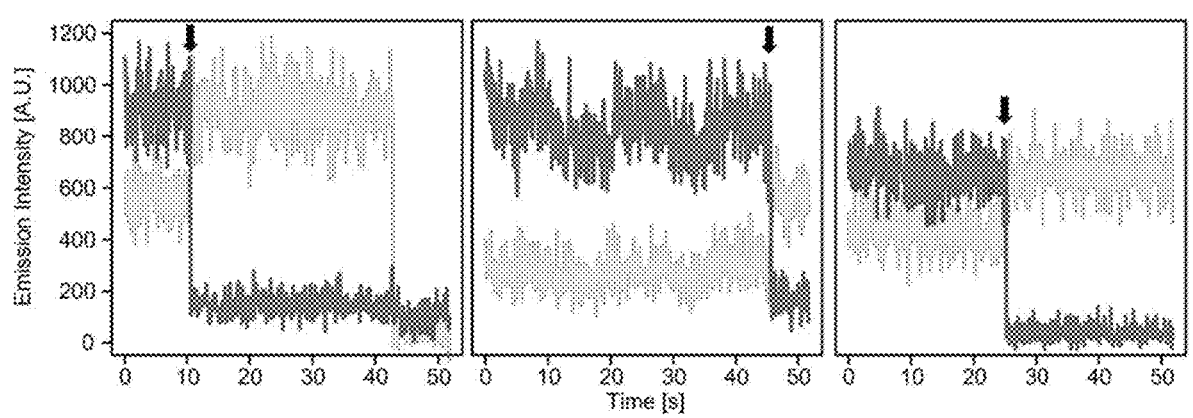

Also constructed were synthetic DNAs with fully-hydroxymethylated (5hmC/5hmCpGs) or fully-methylated CpG sites (5mC/5mCpGs) and verified the smFRET signals were not from these CpG sites (FIG. 3C and FIG. 10). Additionally, mouse cerebellum genomic DNA was used to confirm that the high-FRET events can only be observed in 5mC and 5hmC dual-labeled samples but not in donor-only or acceptor-only single-labeled samples (FIG. 11). Moreover, it was observed anticorrelated intensity changes of the donor and acceptor due to accepter bleaching in mouse cerebellum genomic DNA—a validation of the smFRET events (FIG. 12). These results confirm the existence of high levels 5hmC/5mCpGs in the mouse cerebellum. We further conducted smFRET measurements in genomic DNA from different mouse tissues with different 5hmC levels and cell proliferation rates Ito S, et al. (2011) Tet proteins can convert 5-methylcytosine to 5-formylcytosine and 5-carboxylcytosine. Science 333(6047):1300-1303; Bachman M, et al. (2014) 5-Hydroxymethylcytosine is a predominantly stable DNA modification. Nature Chem. 6(12):1049-1055), and from mouse embryonic stem cell (mESC) as well. Consistently high levels of 5hmC/5mCpGs in all the tissues and cell line were observed, indicating that such hybrid CpG sites are a universal phenomenon across the mammalian genome independent of cell proliferation and 5hmC level (FIG. 3D). After accounting for the efficiency of the labeling and detection on synthetic DNA, it was estimated that 5hmC/5mCpGs roughly account for 60% of 5hmC. The results revise the current understanding that 5hmC mainly exists as fully hydroxymethylated form (5hmC/5hmCpGs) (Pastor W A, Aravind L, Rao A (2013) TETonic shift: biological roles of TET proteins in DNA demethylation and transcription. Nat. Rev. Mol. Cell Biol. 14(6):341-356., Hashimoto H, et al. (2012) Recognition and potential mechanisms for replication and erasure of cytosine hydroxymethylation. Nucleic Acids Res. 40(11):4841-4849) and point to the previously indiscernible 5hmC/5mCpGs as a major state for 5hmC in vivo.

The wide-spread and highly abundant 5hmC/5mCpGs could potentially play important functions such as gene activation and protein binding. One general mechanism of DNA methylation mediated gene repression is through the recruitment of methyl-CpG binding domain (MBD)-containing proteins to fully-methylated CpG sites (Klose R J, Bird A P (2006) Genomic DNA methylation: the mark and its mediators. Trends Biochem. Sci. 31(2):89-97). Being the first intermediate state of TET oxidation of 5mC/5mCpGs, one immediate consequence of 5hmC/5mCpGs could be to inhibit such interactions. Others have investigated MBD binding to asymmetrically methylated sites in the context of oxidative DNA damage (Valinluck V, et al. (2004) Oxidative damage to methyl-CpG sequences inhibits the binding of the methyl-CpG binding domain (MBD) of methyl-CpG binding protein 2 (MeCP2). Nucleic Acids Res. 32(14):4100-4108) and genome replication (Hashimoto H, et al. (2012) Recognition and potential mechanisms for replication and erasure of cytosine hydroxymethylation. Nucleic Acids Res.

Figure 4A:
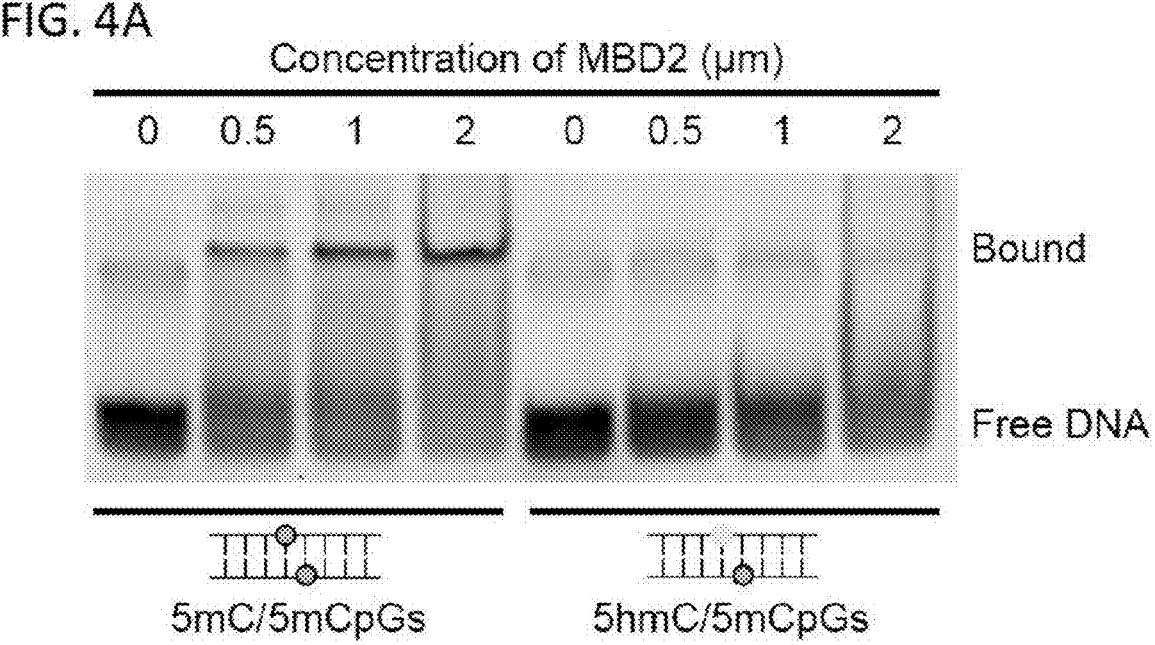
FIG. 4A. 5hmC/5mCpGs shows reduced binding to MBD proteins compared to 5mC/5mCpGs. Binding of 5mC/5mCpGs and 5hmC/5mCpGs containing DNA to varying concentrations of the methyl-CpG binding domain of human MBD2 protein assayed via EMSA.
Figure 4B:
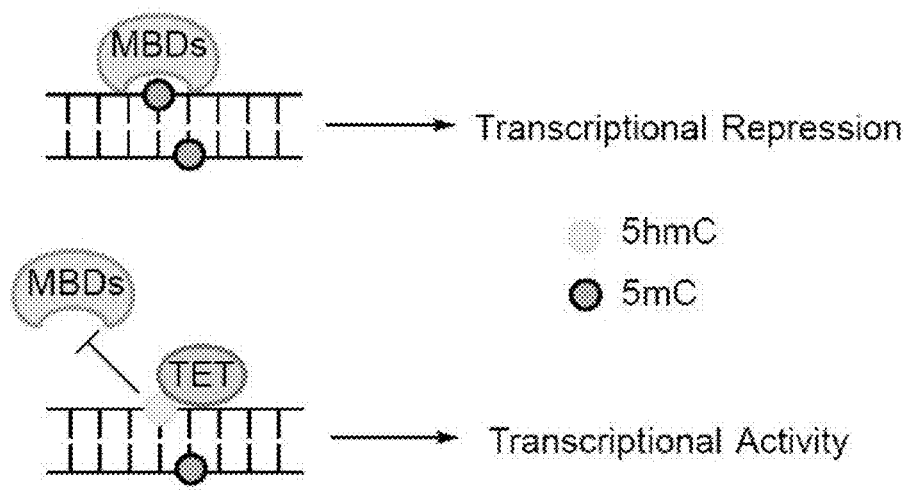
FIG. 4B. 5hmC/5mCpGs shows reduced binding to MBD proteins compared to 5mC/5mCpGs. Model for potential function of 5hmC/5mCpGs in promoting gene expression.

40(11):4841-4849) and found reduced binding affinity. We tested the protein MBD2 using an electrophoretic mobility shift assay (EMSA) on synthetic DNA and found that 5hmC/5mCpGs significantly inhibited its binding compared to 5mC/5mCpGs (FIG. 4A). This result is consistent with previous investigation using other method Hashimoto, supra, and it implies the potential function of 5hmC/5mCpGs may be to induce transcriptional activation through the inhibition of MBD protein binding (FIG. 4B). Future studies are needed to elucidate the functional significance of 5hmC/5mCpGs.

Described herein is a versatile single-molecule technology to image 5mC and 5hmC from trace amounts of DNA The ultra-low input requirement enables this approach to be applied to limited and sensitive samples, such as cell-free circulating DNA (Chan K C, et al. (2013) Noninvasive detection of cancer-associated genome-wide hypomethylation and copy number aberrations by plasma DNA bisulfite sequencing. Proc. Natl. Acad. Sci. U.S.A 110(47):18761-18768). It is also the first measurement technology that can be used to study the co-localization status between 5mC and 5hmC with smFRET. 5mC occurs almost exclusively in the form of 5mC/5mCpGs and is maintained by maintenance methyltransferase DNMT1 following DNA replication. Recent base-resolution sequencing suggested 5hmC to be less symmetric in CpG than 5mC (Yu M, et al. (2012) Base-resolution analysis of 5-hydroxymethylcytosine in the mammalian genome. Cell 149(6):1368-1380). Our results show that a large proportion of 5hmC exists in the form of 5hmC/5mCpGs, a previously undetectable and unappreciated state. TET proteins can convert 5mC in all contexts to 5hmC efficiently in vitro (Zhang L, et al. (2013) Tet mediated covalent labelling of 5-methylcytosine for its genome-wide detection and sequencing. Nat. Commun. 4:1517; Yu M, et al. (2012) Base-resolution analysis of 5-hydroxymethylcytosine in the mammalian genome. Cell 149(6):1368-1380). The wide-spread occurrence of 5hmC/5mCpGs in the mammalian genome suggests TET proteins may be regulated by yet unidentified mechanisms to preferentially oxidize only one strand of 5mC/5mCpGs in vivo. Alternatively, 5hmC/5mCpGs can be generated by the de novo methyltransferase DNMT3 following DNA replication. 5hmC/5mCpGs may play important functions such as gene activation (FIG. 4B) and protein binding, which warrant further investigation. Currently it is believed that this method is the only way to detect such hybrid CpG sites. It highlights the importance of developing new methods that can detect multiple DNA modifications in a same DNA context. Future development and application of this and other single molecule technologies such as the direct detection of DNA modifications by single-molecule, real-time sequencing (Flusberg B A, et al. (2010) Direct detection of DNA methylation during single-molecule, real-time sequencing. Nat. Methods 7(6):461-465) would enable the study of a large set of epigenetic modifications.

It will also be recognized by those skilled in the art that, while the invention has been described above in terms of preferred embodiments, it is not limited thereto. Various features and aspects of the above described invention may be used individually or jointly. Further, although the invention has been described in the context of its implementation in a particular environment, and for particular applications (e.g. epigenetic analysis) those skilled in the art will recognize that its usefulness is not limited thereto and that the present invention can be beneficially utilized in any number of environments and implementations where it is desirable to examine hydroxymethylation and methylation. Accordingly, the claims set forth below should be construed in view of the full breadth and spirit of the invention as disclosed herein.

The ASCII plain text file, submitted via the USPTO patent filing system, identified as "Sequence_Listing," created on May 3, 2022, and having a size of 4 KB, is hereby incorporated by reference in its entirety.

We claim:

1. A method for monitoring ratio changes of 5-hydroxymethylcytosine (5-hmC) residues to 5-methylcytosine (5-mC) residues in two cell-free DNA (cfDNA) samples from a patient obtained at two different time points, comprising:
   (a) providing a first dual-labeled cfDNA sample from the patient at a first time point in which 5-hmC residues are labeled with a first fluorophore and 5-mC residues are labeled with a second fluorophore different from the first fluorophore;
   (b) carrying out single molecule fluorescence microscopy on the first dual-labeled cfDNA sample by irradiating the first dual-labeled cfDNA sample with a dual-laser excitation system, exciting the first fluorophore of the first dual-labeled cfDNA at a first wavelength and exciting the second fluorophore of the first dual-labeled cfDNA at a second wavelength, and quantifying a first fluorescent signal produced from the first fluorophore of the first dual-labeled cfDNA and quantifying a second fluorescent signal produced from the second fluorophore;
   (c) calculating a first 5-hmC level and a first 5-mC level in the first dual-labeled cfDNA based on counts of the first fluorescent signal produced from the first fluorophore of the first dual-labeled cfDNA and counts of the second fluorescent signal produced from the second fluorophore of the first dual-labeled cfDNA, and determining a first ratio of 5-hmC residues to 5-mC residues in the first dual-labeled cfDNA sample;
   (d) obtaining a second dual-labeled cfDNA sample from the patient at a second time point later than the first time point, the second dual-labeled cfDNA sample having 5-hmC residues labeled with the first fluorophore and 5-mC residues labeled with the second fluorophore; and
   (e) determining a second ratio of 5-hmC residues to 5-mC residues in the second dual-labeled cfDNA sample by repeating steps (b) and (c) with the second dual-labeled cfDNA sample, thereby monitoring the ratio changes of 5-hmC residues to 5-mC residues in the two cell-free DNA (cfDNA) samples from the patient obtained at the two different time points.

2. The method of claim 1, wherein one of the first fluorophore and the second fluorophore is a fluorescence resonance energy transfer (FRET) donor and the other of the first fluorophore and the second fluorophore is a FRET acceptor, and the method further comprises determining a first single-molecule fluorescence resonance energy transfer (smFRET) between the FRET donor and the FRET acceptor at the first time point and a second smFRET between the FRET donor and the FRET acceptor at the second time point.

3. The method of claim 2, wherein two peaks in the first smFRET represent a peak of 5-hmC residues and a peak of 5-mC residues in the first dual-labeled cfDNA and there is a distance between the two peaks in the first smFRET, two peaks in the second smFRET represent a peak of 5-hmC residues and a peak of 5-mC residues in the second dual-labeled cfDNA and there is a distance between the two peaks in the second smFRET, and the method further includes comparing the second distance to the first distance.

4. The method of claim 1, wherein the first dual labeled cfDNA sample and the second dual labeled cfDNA sample comprise 50 picograms of DNA or less than 50 picograms of DNA.

* * * * *

SEQUENCE LISTING

```
<160> NUMBER OF SEQ ID NOS: 10

<210> SEQ ID NO 1
<211> LENGTH: 36
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (6)..(6)
<223> OTHER INFORMATION: N is a 5-Methylcytosine (5mC)
<220> FEATURE:
<221> NAME/KEY: Misc_feature
<222> LOCATION: (29)..(29)
<223> OTHER INFORMATION: N is a 5-hydroxymethylcytosine (5hmC)

<400> SEQUENCE: 1
cccgangcat gatctgtact tgatcgacng tgcaac                                36

<210> SEQ ID NO 2
<211> LENGTH: 36
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(1)
```

<223> OTHER INFORMATION: linked to a biotin at the 5' end

<400> SEQUENCE: 2
gttgcacggt cgatcaagta cagatcatgc gtcggg         36

<210> SEQ ID NO 3
<211> LENGTH: 36
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_Feature
<222> LOCATION: (19)..(19)
<223> OTHER INFORMATION: N is a 5-Methylcytosine (5mC)
<220> FEATURE:
<221> NAME/KEY: Misc_Feature
<222> LOCATION: (29)..(29)
<223> OTHER INFORMATION: N is a 5-hydroxymethylcytosine (5hmC)

<400> SEQUENCE: 3
cccgacgcat gatctgtant tgatcgacng tgcaac         36

<210> SEQ ID NO 4
<211> LENGTH: 36
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(1)
<223> OTHER INFORMATION: linked to a biotin at the 5' end

<400> SEQUENCE: 4
gttgcacggt cgatcaagta cagatcatgc gtcggg         36

<210> SEQ ID NO 5
<211> LENGTH: 36
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (6)..(6)
<223> OTHER INFORMATION: N is a 5-Methylcytosine (5mC)
<220> FEATURE:
<221> NAME/KEY: Misc_feature
<222> LOCATION: (8)..(8)
<223> OTHER INFORMATION: N is a 5-hydroxymethylcytosine (5hmC)

<400> SEQUENCE: 5
cccgangnat gatctgtact tgatcgaccg tgcaac         36

<210> SEQ ID NO 6
<211> LENGTH: 36
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(1)
<223> OTHER INFORMATION: linked to an biotin at the 5' end

<400> SEQUENCE: 6
gttgcacggt cgatcaagta cagatcatgc gtcggg         36

```
<210> SEQ ID NO 7
<211> LENGTH: 36
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (18)..(18)
<223> OTHER INFORMATION: N is a 5-Methylcytosine (5mC) or a
      5-hydroxymethylcytosine (5hmC)

<400> SEQUENCE: 7
tcgatgtagt gcgtcacngg atgatagctg tactca                               36

<210> SEQ ID NO 8
<211> LENGTH: 36
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(1)
<223> OTHER INFORMATION: linked to a biotin at the 5' end
<220> FEATURE:
<221> NAME/KEY: Misc_feature
<222> LOCATION: (18)..(18)
<223> OTHER INFORMATION: N is a 5-Methylcytosine (5mC) or a
      5-hydroxymethylcytosine (5hmC)

<400> SEQUENCE: 8
tgagtacagc tatcatcngg tgacgcacta catcga                               36

<210> SEQ ID NO 9
<211> LENGTH: 36
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (18)..(18)
<223> OTHER INFORMATION: N is a 5-Methylcytosine (5mC) or a
      5-hydroxymethylcytosine (5hmC)

<400> SEQUENCE: 9
tcgatgtagt gcgtcacngg atgatagctg tactca                               36

<210> SEQ ID NO 10
<211> LENGTH: 36
<212> TYPE: DNA
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (1)..(1)
<223> OTHER INFORMATION: linked to a FAM at the 5' end
<220> FEATURE:
<221> NAME/KEY: Misc_feature
<222> LOCATION: (18)..(18)
<223> OTHER INFORMATION: N is a 5-Methylcytosine (5mC)

<400> SEQUENCE: 10
tgagtacagc tatcatcngg tgacgcacta catcga                               36
```